United States Patent [19]

Connelly et al.

[11] Patent Number: 5,597,688
[45] Date of Patent: Jan. 28, 1997

[54] CELL FIXATIVE AND METHOD OF ANALYZING VIRALLY INFECTED CELLS

[75] Inventors: Mark C. Connelly, Doylestown, Pa.; Utpal R. Chakraborty, Flemington; Houston G. Brooks, Jr., Somerset, both of N.J.

[73] Assignee: Ortho Diagnostic Systems Inc., Raritan, N.J.

[21] Appl. No.: 467,799

[22] Filed: Jun. 6, 1995

Related U.S. Application Data

[62] Division of Ser. No. 859,212, Mar. 27, 1992, Pat. No. 5,422,277.

[51] Int. Cl.$^6$ .............................. C12Q 1/70; G01N 33/53; G01N 33/569
[52] U.S. Cl. .............................. 435/5; 435/7.1; 435/7.24; 435/975; 530/388.2
[58] Field of Search .............................. 435/5, 7.1, 7.2, 435/7.24; 436/501, 800, 807; 530/387.1, 388.1, 388.3, 388.7, 389.1, 389.6, 388.2

[56] References Cited

U.S. PATENT DOCUMENTS

| | | | |
|---|---|---|---|
| 4,423,153 | 12/1983 | Ranney et al. | 436/63 |
| 4,499,183 | 2/1985 | Sujansky et al. | 435/6 |
| 4,632,907 | 12/1986 | Sato et al. | 436/10 |
| 4,698,312 | 10/1987 | Wong et al. | 436/10 |
| 4,933,293 | 6/1990 | Kuroda et al. | 436/63 |
| 5,422,277 | 6/1995 | Connelly et al. | 436/10 |

FOREIGN PATENT DOCUMENTS

| | | | |
|---|---|---|---|
| 0175371 | 3/1986 | European Pat. Off. | G01N 1/30 |
| 3824936 | 3/1990 | Germany | G01N 1/28 |
| 552538 | 4/1977 | U.S.S.R. | G01N 1/30 |
| 2192712 | 1/1988 | United Kingdom | G01N 1/28 |

OTHER PUBLICATIONS

H. Sumner et al., Journal of Immunological Methods, 136 (1991), pp. 259–267.
L. Zamboni et al., The Journal of Cell Biology, vol. 35, 1967, p. 148 A.
The Chemistry and Practice of Fixation, pp. 97–158.

*Primary Examiner*—Mary E. Mosher
*Assistant Examiner*—Henry E. Auer

[57] ABSTRACT

The present invention provides a novel cellular fixative composition and method of cellular fixing and cellular analysis wherein cells may be fixed for further analysis without destroying the cell's surface markers, cellular morphology, and the cell's light scattering properties. Treatment of cells with the fixative as described herein also allows antibodies or other desired components to enter the cell through the cellular membrane, without allowing important contents of the cell to escape. As an added benefit, the fixative composition of the invention may also kill or at least inactivate or reduce the activity of deadly virus contained in the cell. In its broadest aspect, the presently claimed fixative composition comprises at least three components, and in more preferred embodiments, four components. In a particularly preferred embodiment, the fixative composition described herein comprises at least one compound suitable for increasing the permeability of a cellular membrane, at least one compound that facilitates transportation of components across cellular membranes, at least one detergent, and at least one compound having the structure:

$$R_1R_2R_3R_4R_5\text{—Ar—X}$$

9 Claims, 6 Drawing Sheets

NO. OF CELLS

LOG OF p24 STAINING INTENSITY

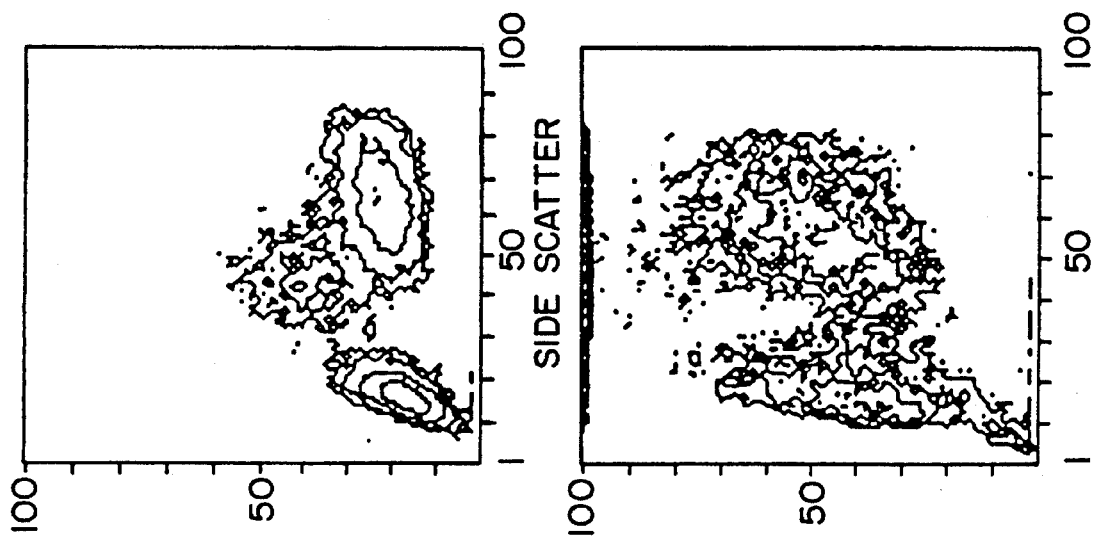
FIG.6c ANTI-p24 STAINING INTENSITY
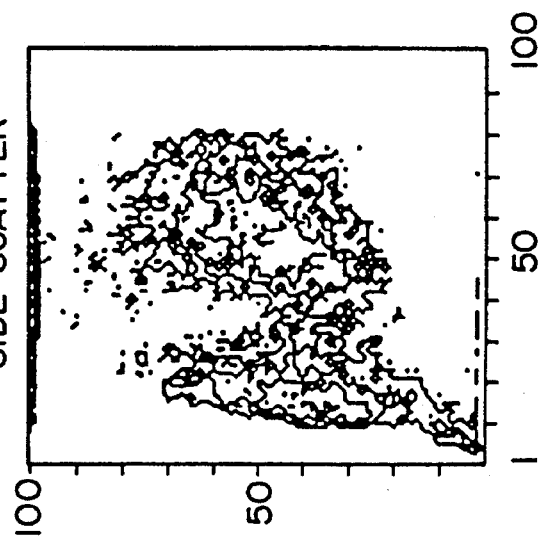
FIG.6d ANTI-p24 STAINING INTENSITY
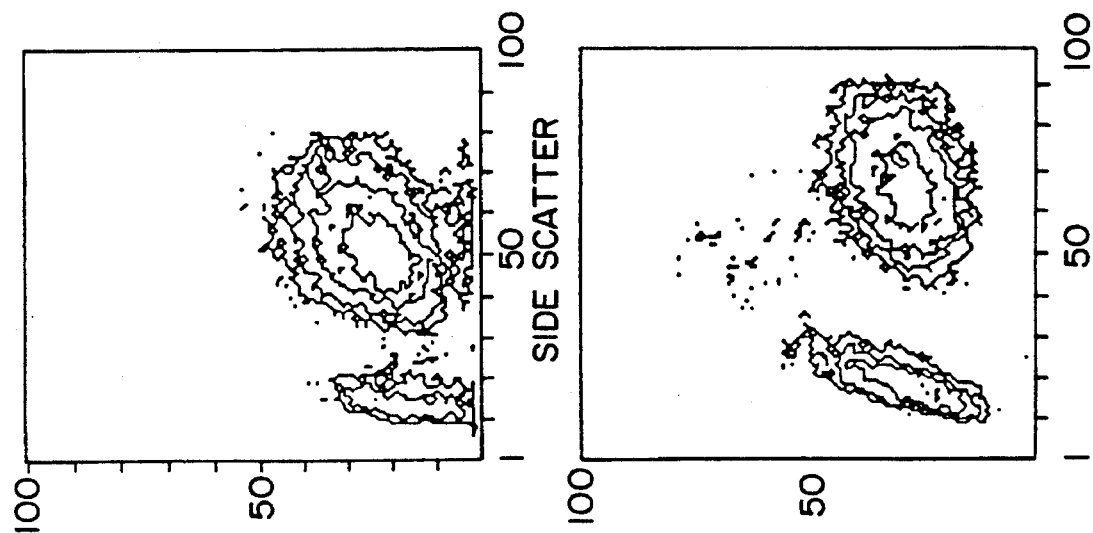
FIG.6a ANTI-p24 STAINING INTENSITY
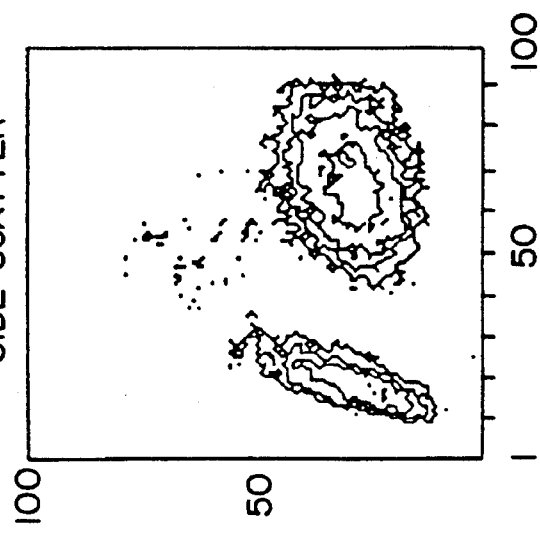
FIG.6b ANTI-p24 STAINING INTENSITY

CELL FIXATIVE AND METHOD OF ANALYZING VIRALLY INFECTED CELLS

This is a division of application Ser. No. 07/859,212, filed Mar. 27, 1992, now U.S. Pat. No. 5,422,277 which is hereby incorporated by reference.

The present invention relates to a cell fixative that allows the user to fix the cells, without substantially destroying cellular properties such as the cell's surface markers, morphology, and light scattering properties. In certain preferred embodiments, use of such a fixative composition would allow antibodies or other components of interest to enter into the cell, by rendering the cellular membrane permeable to these relatively large components, without releasing the cellular contents. The fixative and methods of cellular analysis described herein are particularly useful in the staining of cells to determine whether or not they are infected with a virus, the extent of such infection, and whether or not a patient is responding to treatment for a virus infection by the monitoring of that patient's blood cells for certain parameters of viral infection.

BACKGROUND OF THE INVENTION

Since the outbreak of AIDS and other viral-related disease states there has been an increased need for new and better methods of studying the etiology and pathology of viruses, as well as therapeutic monitoring of treatment regimes for arresting or modifying in some way the effect these viruses have on cells, and ultimately the patient. For example, it is often desirable to assay the percentage of cells infected. A high virus burden usually means the disease is rampant, while a low virus burden might mean that the particular disease is in its early stages, or is responding to therapeutic treatment, and so on. Conventional assays for measuring virus burden have to date been merely extrapolative in nature. For example, cells may be cultured and titrated out for analysis. In these assays, it is common to employ polymerase chain reaction amplification techniques, in an attempt to quantitate copies of DNA (as the provirus form) or RNA present, the precept being, the more RNA, the more virus. However, results obtained with techniques of this sort can only indicate without distinction, a small quantity of infected cells having a high quantity of virus burden, or a larger quantity of cells with a low virus burden per cell. Another drawback is that a determination in accordance with this technique does not provide information as to whether or not the virus infection is replicative or abortive, since one does not know "how many" or "which" cells are infected. Hence, true virus burden assessment, as well as virus activity cannot be had with this technique. Furthermore, it is difficult, cumbersome, and costly to implement, all without giving results that are acceptable in sensitivity.

Virus infection may also be monitored by monitoring the quantity of a viral component such as p24 (in the case of HIV-1) present in a patient's serum. However, this technique is grossly extrapolative and often given to false negatives. For example, a patient may demonstrate a short spike in p24 concentration at the beginning of infection, when the virus is replicating, but before that patient's antibody response to this virus. Within a period of 5 days to about 2–3 weeks, the patient will start to make antibodies to p24. These antibodies bind to the p24 in plasma and either remove it from circulation or block its detection in immunoassays. Accordingly, there is a very short window in which to detect the p24 antigen component, as the patient will test negative once he is making antibodies to the p24. It is not until the patient becomes so compromised that he can no longer produce antibodies to the p24 component, that the test begins to again indicate a positive result for the p24 antigen. Unfortunately, the patient prognosis is very grim at this point, as the disease has progressed past the stage of responding to any therapeutic treatment.

Hence, there is a continuing need for better tools and techniques for measuring viral burden in cells, and the viability and replicability of the virus in those cells. This information is invaluable in determining the progress of the viral infection and its response to treatment. Further, there is a definite need to monitor these parameters at a very early stage in the disease progression, and to continue this monitoring unimpeded throughout the path of infection.

In particular, there is a specific need for routine monitoring of virus load in HIV-infected individuals, preferably, through the use of a fixative that inactivates the virus and thus, increases the safety of handling samples containing this deadly virus. This information will be used by physicians to categorize HIV disease states, monitor and document progression, assess prognosis, and possibly to better tailor effective therapeutic regiments on an individual basis. Additionally, pharmaceutical companies and researchers require just such an assay for use in clinical trials, to determine rapidly if a proposed therapeutic agent is both safe and effective at controlling virus load.

By way of background in cell analysis techniques useful in monitoring a patient, it is noted that conventional flow cytometry is a technique quite suitable for such a task. The fundamental concept of flow cytometry is that cells or subcellular components in aqueous suspension are made to flow at high speed through a sensing region where optical or electrical signals indicative of important biologic properties are generated. These signals are analyzed and accumulated for evaluation. The cells may be fluorescently stained, although other dye systems may be employed, (see U.S. Pat. No. 4,933,293) and no staining is necessary for light-scatter measurements or electrical sizing. Generally, hydrodynamic methods are used to force the cells to move in almost identical trajectories at uniform speeds through a focal spot of intense illumination capable of exciting fluorescent emission from the fluorochrome used. A laser is the typical light source. The cell receives uniform illumination for a very short period of time and emits a burst of fluorescence and scattered light of this duration over all angles. A fraction of the light emission per cell is captured by an optical arrangement and one or more photosensors generating electrical signals proportional to the optical signals. Since the fluorescent light emission occurs at longer wavelength than the incident light while the scattered light experiences no wavelength change, these two signals can be separated with filters and measured independently and simultaneously for each cell. The electrical pulses are shaped, amplified, measured, and either displayed or stored for later analysis. Flow sorting can also be accomplished, to sort different cellular populations from a sample. Typically, the cell suspension is forced out of a tiny orifice and forms a high-speed liquid jet in air. Optical sensing is usually done in the jet in air close to the orifice outlet, and is basically identical to the method used in the flow cytometer just described. Applied ultrasonic vibration causes breakup of the jet into uniform droplets, which traverse a region of high (and constant) electric field intensity. Decision-making and charging circuits electrically charge only droplets containing selected cells; droplets containing unwanted cells and empty droplets remain uncharged. The electric field deflects the charged droplets, which contain the desired cellular subpopulation, into one container while all the other droplets go to another container. In this way specific subpopulations of high purity can be obtained for further biologic study, such as morphologic or biochemical analysis (The above paragraph is taken from: *Flow cytometry and Sorting*, Melamed et al. editors, John Wiley and Sons, 1979, pp.11–14).

The above-described technique may be used with a patient's cells, to analyze for the presence of viral antigens. Interfering antibodies present in such patient's blood sample are simply washed away with the serum prior to this flow cytometric analysis. However, virion particles, if present, are in the cellular cytoplasm, and sometimes the nucleus. In order to look at the viral antigens inside the cell, the cellular membrane must be permeated to allow antibodies against the virus to enter the cell. Using the prior art techniques of the past, all or a portion of the cellular surface would be stripped away to allow the large antibody to enter. Typically this is done through the use of agents such as methanol or other alcohols which tend to extract lipids and precipitate proteins. Such agents basically turn the cell into a bead of protein, and in this manner provide access to the proteins that may be present. However, in so doing, the cell's surface characteristics are destroyed.

The present invention provides a cellular fixative and fixing technique which fixes cells without substantially destroying that cell's cellular surface characteristics, all the while allowing large molecules, such as antibodies, to enter the cell. This is accomplished without the concomitant release of the virion particles from the inner cell. Thus, a single treatment reagent is provided herein, which is capable of permeating the cell and fixing it, while preserving both the immunoreactivity and light scatter of such cell. The fixative and method of cellular analysis described herein is particularly well-suited for use in flow cytometry analysis.

SUMMARY OF THE INVENTION

The present invention provides a novel cellular fixative composition and method of cellular analysis comprising at least one:

I. compound of the General Structure:

Wherein:
$X = SO_3H$, $SO_2NH_2$, $SO_2NHR$, $SO_2NR_2$, $SO_2OR$, $SO_2OAr$, $SO_2NHC_6H_5$, $SO_2N(C_6H_5)_2$, COOH, COOR, $COOC_6H_5$, COOAr, CN, OH, OR, OCOR, $OCONH_2$, OCONHR, $OCONR_2$, OCONHAr, $OCONAr_2$;

R=H or alkyl chain containing 1–6 carbon atoms;

Ar=one to three aromatic rings, fused or non-fused and either the same or different, and comprising benzene rings, heterocyclic rings or rings containing one or more heteroatoms either the same or different, which is (are) nitrogen (N), oxygen (O) or sulphur (S), said rings substituted with $R_1$, $R_2$, $R_3$, $R_4$, and $R_5$;

$R_1, R_2, R_3, R_4, R_5$ =are either the same or different, and are $NO_2$, COR, COOR, COOH, $CONH_2$, CONHR, $CONR_2$, CHO, X, OH, OR, Ar, R, or $CF_3$.

In preferred embodiments, the fixative composition further comprises at least one:
II. alcohol-free cellular fixative;
III. at least one compound suitable for increasing the permeability of a cellular membrane; and/or
IV. at least one compound that facilitates transport of components across cellular membranes.

In certain most preferred embodiments, a fixative composition comprising one or more components selected from each of the four above-mentioned categories is provided, especially when the alcohol-free cellular fixative component is high-grade formaldehyde, and the compound to facilitate transport across the cellular membrane component is dimethylsulfoxide. Also provided are methods of cellular analysis wherein a cell sample is fixed with the fixative composition as described herein, and the cells so fixed are then interrogated with labeled binding ligands to detect the presence or absence of various cell surface markers and/or intracellular components, and especially when that cellular analysis is accomplished through the use of flow cytometry. Results obtained using the aforementioned cell analysis may be applied to disease diagnosis and monitoring.

BRIEF DESCRIPTION OF THE DRAWINGS

FIGS. 6a, 6b, 6c, and 6d are contour plots, obtaining on a FACScan, showing the results of staining of blood from three HIV-infected patients (6b, 6c, and 6d), in three various stages of disease infection, and the results obtained with a sample from a control, noninfected hospital patient (6a).

DETAILED DESCRIPTION OF THE INVENTION

Figure 1:
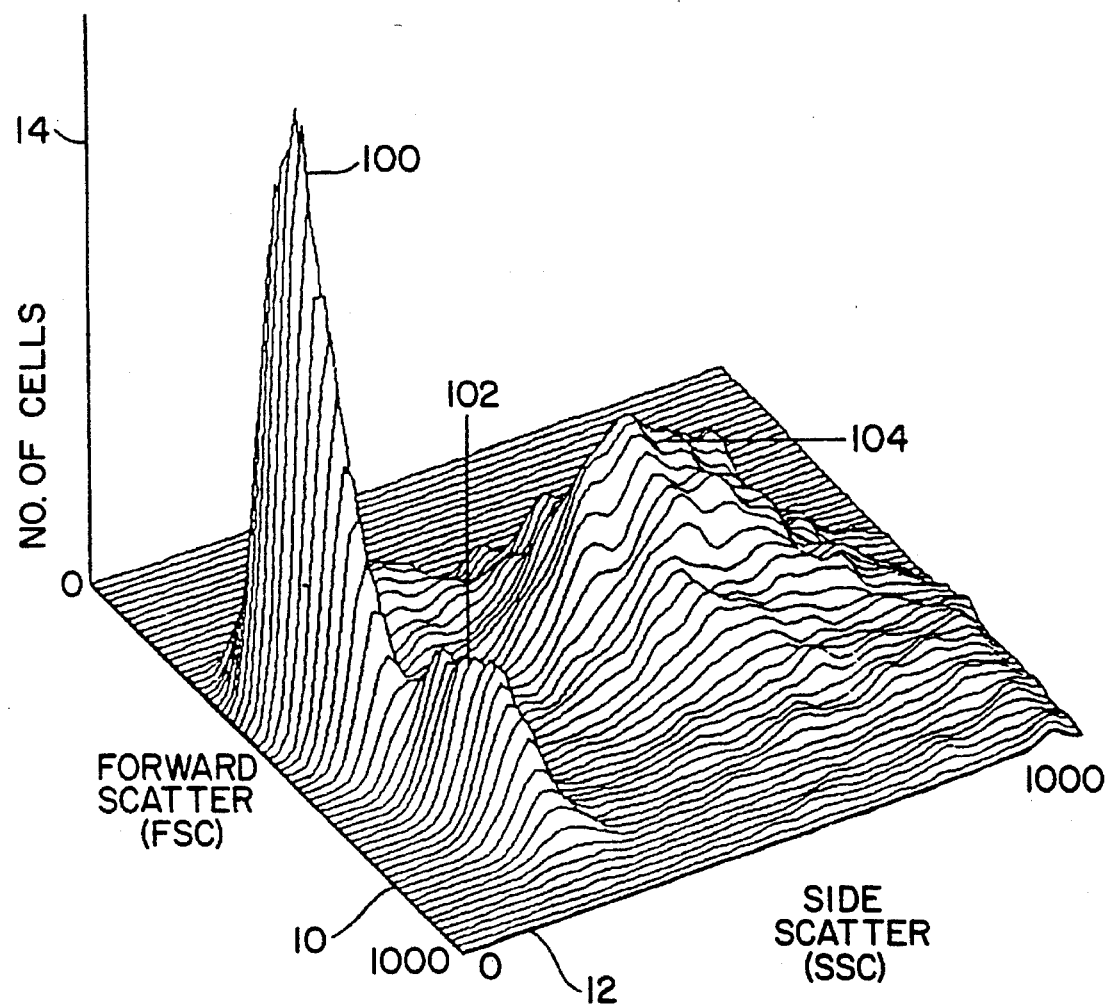
FIG. 1 is a three-dimensional plot obtained with the use of a FACScan flow cytometer demonstrating the distribution of white blood cell clusters in a live, unfixed cell population.

The present invention provides a novel cellular fixative composition, method of cellular fixing and cellular analysis, method of viral burden monitoring and monitoring of disease progression in a patient, as well as reagents useful therefore. Cells may be fixed for further analysis without substantially destroying the cell's cellular properties such as surface markers, cellular morphology, and the cell's light scattering properties. Treatment of cells with the fixative as described herein also allows antibodies or other desired components to enter the cell through the cellular membrane, without allowing a substantial amount of the contents of the cell to escape. Cells fixed with the composition of the invention, although dead, frequently demonstrate properties during cellular analysis that are very similar to those demonstrated by "live cells". For example, the differentiation of cell types based on their light scatter properties is still intact. Further, the morphology is very similar to that of live cells, with much less swelling and shrinkage than is typically displayed by fixed cells. In sum, one can often analyze the cells fixed in accordance with the present invention in much the same manner as one would analyze a live cell population.

In its broadest aspect, the presently claimed fixative composition comprises at least one component that will serve to fix a cell's cytoplasm quickly, so as to maintain the integrity of the cellular contents in their normal position, without major disruption. This is almost analogous to "freezing" the cytoplasm in place. One or more compounds suitable for this purpose may be selected from the following classes of aromatic compounds:

A compound of the General Structure:

Wherein:
X=$SO_3H$, $SO_2NH_2$, $SO_2NHR$, $SO_2NR_2$, $SO_2OR$, $SO_2OAr$, $SO_2NHC_6H_5$, $SO_2N$ $(C_6H_5)_2$, COOH, COOR, $COOC_6H_5$, COOAr, CN, OH, OR, OCOR, $OCONH_2$, OCONHR, $OCONR_2$, OCONHAr, $OCONAr_2$;
R=H or Alkyl chain containing 1–6 carbon atoms
Ar=one to three aromatic rings, fused or non-fused, either the same or different, and comprising benzene rings, heterocyclic rings or rings containing one or more heteroatoms either the same different, which is (are) N, O, or S, said rings substituted with $R_1$, $R_2$, $R_3$, $R_4$, and $R_5$; and $R_1,R_2,R_3,R_4,R_5$=are either the same or different, and are $NO_2$, COR, COOR, COOH, $CONH_2$, CONHR, $CONR_2$, CHO, X, OH, OR, Ar, R or $CF_3$.

The fixative composition may comprise one or a combination of compounds selected from those having this General Structure.

In more preferred embodiments the fixative composition may comprise one or a combination of compounds selected from those having the General Structure and wherein:
$R_1,R_2,R_3$=one, two or three groups, each either the same or different, and is (are)—$NO_2$, COR, COOR, COOH, $CONH_2$, CONHR, $CONR_2$, CHO, $SO_3H$, $SO_2NR_2$, $SO_2NHR$, $SO_2NHAr$, OH, OR, $CF_3$, or R.

In certain other preferred embodiments, $R_1R_2R_3$=one, two, or three groups, each either the same or different, and is (are) $NO_2$, COR, COOR, COOH, $CONH_2$, CHO, $SO_3H$, $SO_2NHR$, $SO_2NR_2$, $SO_2NHAr$, OH, OR, or R, with the proviso that $R_3$ is not $NO_2$ when $R_1$ and $R_2$ are $NO_2$. Explosive and other undesirable properties are inherent in tri-substituted $NO_2$ compounds, and it is therefore preferable to avoid this substitution in certain instances, unless the undesirable properties can be neutralized in some way.

In particularly preferred embodiments, X is $SO_3H$, COOH, or OH, and $R_1$, $R_2$, $R_3$ are the same or different and are $NO_2$, COOR, COOH, $CONH_2$, CONHR, $CONR_2$, CHO, OH, R, or X, with the proviso that when $R_1$ and $R_2$ are $NO_2$, then $R_3$ is other than $NO_2$.

Particularly preferred compounds belonging to this generic class are 2,4-Dinitrobenzene sulfonamides, Dinitrophenols, 3,5-Dinitrosalicylic acid, 2,4-Dinitrobenzoic acid, 5-Sulfosalicylic acid, 2,5-Dihydroxy-1,4-benzene disulfonic acid, 3,5-Dinitrobenzoic acid, 8-Hydroxyquinoline-5-sulfonic acid, 4-Nitrophenol, 3,5-Dinitrosalicylaldehyde, 3,5-Dinitroaniline, Paratoluene sulfonic acid, 2-Mesitylene sulfonic acid, 2-(Trifluoromethyl) benzoic acid, 3,5-Dinitrobenzonitrile, and 2,4-Dinitrobenzene sulfonic acid. More particularly preferred are Dinitrobenzaldehyde, Dinitrobenzene sulfonic acids, Dinitrobenzoic acids, and specifically 3,5-Dinitrobenzoic acid, 2,4-Dinitrobenzoic acid, 2,4-Dinitrobenzene sulfonic acid, 2,6-Dinitrobenzene sulfonic acid, 3,5-Dinitrobenzene sulfonic acid, and 2,4-Dinitrophenol.

Preferred embodiments of the fixative composition of the invention comprise one or any combination of said aforementioned compounds, dissolved or otherwise dispersed in a vehicle that is compatible with the compound and cells and is suitable to make a homogeneous liquid composition containing such one or more compounds.

A substantial number of species belonging to this generic class of compounds may be obtained commercially from such chemical suppliers as Aldrich Chemicals (Milwaukee, Wis.), Fluka (Switzerland), Janssen (New Jersey and Belgium), Eastman-Kodak (Rochester, N.Y.), Lancaster Chemicals (Windham, N.H.), and other such fine chemical suppliers. One skilled in the art of organic synthesis will also understand that these compounds may be chemically synthesized de novo, or in part if intermediates to this component are first obtained commercially from suppliers as mentioned above. Suitable techniques for chemical syntheses of these types are described in such treatises as "Synthetic Organic Chemistry", by Wagner and Zook, John Wiley & Sons, Inc., New York, 1953; "Chemistry of Carbon Compounds", by Rodd, Elsevier Publishing Co., Amsterdam, 1954 (vol. III, part A).; "The Organic Chemistry of Sulfur" by Chester M. Suter, John Wiley & Sons, Inc., New York, 1944; "Organic Syntheses", John Wiley & Sons, Inc. New York, to name but a few. One skilled in the art will understand that in many cases, the chemical name of a compound one desires to synthesize may be looked up in the table of contents or index of such treatises or lab manuals, for the correct page in the volume detailing that compound's synthesis. In most cases, the original papers describing the various syntheses are included in the bibliography sections of such works, and may also be consulted if desired.

In more preferred embodiments, the fixative composition of the invention comprises a second component. The second component of the fixative composition of the invention is one, or a combination of alcohol-free compounds, each of which is generally described in the art as a "fixative", and which acts by attaching to proteins and cementing their structure. The cementing mechanism of action accorded to these alcohol-free compounds may vary, and includes reaction of free amines, reaction with lipids, or cross-linking of the protein. Of these fixatives may be mentioned singly or in any combination formaldehyde, paraformaldehyde, glutaraldehyde, acrolein, glyoxal, malonaldehyde, diacetyl, polyaldehydes, carbodiimides, diisocyanates, diazonium compounds, diimido esters, diethylpyrocarbonate, maleimides, benzoquinone, metallic ions and other complexes such as chromium, mercury, osmium tetroxide, palladium chloride, uranium, and the like. Preferred as the component for inclusion in the fixative composition of the present invention are one or more amine reactive aldehydes such as glutaraldehyde, acrolein, formaldehyde, paraformaldehyde, and the like. Especially preferred is a high grade alcohol-free formaldehyde. One skilled in the art will understand that the above-mentioned components are commercially available through such vendors, inter alia, as Sigma Chemicals in St. Louis, Mo., Polysciences of Warrington, Pa., Aldrich Chemical of Milwaukee, Wis., and the like. A useful treatise for the chemistry of these and other commonly known fixatives may be found in *The Chemistry and Practice of Fixation*, from Histochemistry Theoretical and Applied, A. G. Everson Pearse, Vol. 1, 4th Edition, Publishers Churchill Livingstone, Edinburgh, London & New York, 1980, pp. 97–158. Concentrations of the subject components are those concentrations generally used in the fixation of tissue, and concentrations preferably a little less than generally used, so as to afford a more "gentle" fixation. For example, in the case of the reactive aldehydes, preferred concentrations in percent as measured by weight per volume are generally about 0.1% (w/v) to about 4% (w/v). More preferred concentrations are about 0.2% (w/v) to about 2% (w/v) and particularly preferred concentrations range from about 0.5% (w/v) to about 1.6% (w/v).

In most preferred embodiments of the fixative composition of the invention, a third or even fourth component is added. The third component of the fixative composition of the present invention is a compound or combination of compounds selected from one of two groups of compounds. The first group may be functionally described as those compounds that facilitate transport of components across cellular membranes. The second group may be described as a detergent or surfactant, such as a non-ionic detergent. In the most particularly preferred embodiments, the fixative composition comprises at least one component from each of these two categories, totaling four separate components in all.

Of the compounds that facilitate transport of components across the cell membrane, may be mentioned those that decrease the surface potential of lipid monolayers. Of these, may be mentioned water-soluble or water-insoluble "fusogenic" compounds, such as dimethylsulfoxide, sulfolane, 1-methyl-2-pyrrolidinone, polyethylene glycol (PEG), ethyleneglycol, and the like. This component generally renders the cellular membrane more permeable to low molecular weight compounds, and facilitates entry of such compounds into the cell's cytoplasm, at the same time it prevents the cell from swelling. The previously described components, namely the fixative component and the component of General Formula I, can then enter rapidly and fix the contents of the cell before they could spill out in any substantial measure. Preferred among the compounds that facilitate transport across the cell membrane is dimethylsulfoxide, because it is less fusogenic than some compounds that promote transport across a membrane, has less of an effect on light scatter, is stable, and does not react to any great extent with the other components of the fixative. Suitable concentrations are those concentrations that will not cause membrane fusion in substantial measure. Preferred concentrations range from about 1% (v/v) to about 20% (v/v), with about 5% (v/v) to about 15% (v/v) especially preferred.

Suitable detergents to serve as either the third or fourth component of the fixative composition are one or a combination of detergents that will render the cellular membrane permeable to large molecules of about 200 kD to about 1000 kD, and especially large molecules generally described as binding ligands useful in binding to and thus detecting cell surface markers or intracellular components, and the like. Good examples of such binding ligands are labeled antibodies, labeled DNA and RNA probes, specific substrates, co-factors, and the like. Typical labels for such binding ligands are fluorescent compounds such as the phycobiliproteins (including phycoerythrin), and fluorescein isothyocyanate (FITC), radioactive labels, enzymatic, biotin-avidin labels, and the like, all well known to the art. Accordingly, the detergent or combination of detergents should be capable of permeating the cell surface to the degree necessary to accommodate entry of a molecule of this size. However, this component should accomplish permeation at a concentration that will enable it to act in concert with the other components of the fixative composition, so as to avoid, in substantial measure, extraction of lipids or other components from the cell's interior. If too much of the cellular components of a cell's interior is extracted, the light-scattering properties of the cell will be detrimentally affected.

Preferred for use herein as this third or fourth component, are one or a combination of zwitterionic or non-ionic surfactants such as sodium cholate, deoxycholates, CHAPS, saponin, and polymers of ethylene oxide, such as ethoxylated alcohols, ethoxylated alkyl phenols, ethoxylated amines and amides, polyoxyethylene sorbitans of the "Tween™" series, such as monolaurate (Tween 20), monopalmitate (Tween 40), monooleate (Tween 80), and polyoxyethylene 23 lauryl ether (BriJ™ 35), polyoxyethylene ether W-1 (Polyox), and the like. One skilled in the art will understand that a good description of compounds belonging to the foregoing classifications, and vendors from whom such compounds may be commercially obtained may be found in "Chemical Classification, Emulsifiers and Detergents", *McCutcheon's, Emusifiers and Detergents,* 1986, North American and International Editions, McCutcheon Division, MC Publishing Co., Glen Rock, N.J., U.S.A. and Judith Neugebauer, *A Guide to the Properties and Uses of Detergents in Biology and BioChemistry,* Calbiochem®, Hoechst Celanese Corp., 1987. Preferred among these are the polyoxyethylene sorbitans of the "Tween™" series available from Sigma Chemicals, or the Triton™ series, available from Rohm and Haas of Philadelphia, Pa., and especially Triton™ X-705, Triton™ X-100, and Triton™ X-114, available commercially from many vendors. Preferred concentrations of these range from about 0.001 to about 0.2% (w/v), with about 0.05 to about 0.1% (w/v) particular preferred.

The fixative composition of the invention is prepared by selecting one or more components as described herein, and then physically dispersing the desired one or more components into a suitable buffer or other liquid vehicle, such as a isotonic medium. Examples of such suitable vehicles include phosphate buffered saline, saline, MOPS, HEPES, HEPPES, Hank's Balanced Salt Solution, RPMI, and the like. Denaturation or deformation of the cells should be avoided and a concentration of the compound in the vehicle should be that which is suitable to fix cells in accordance with the techniques described herein. The components should be dispersed homogeneously or actually solubilized in the liquid vehicle. Amounts of the various components of the fixative composition, as chosen in accordance with the details above, are combined in a suitable vessel under mixing conditions. One skilled in the art may routinely choose the sequence in which each component is added to the mixture. For example, in the most particularly preferred embodiments, a phosphate buffered solution is first added to the vessel under conditions of continuous mixing followed by DMSO, DNBS (as a solid), Tween™, and formaldehyde. This sequence of addition of components to prepare the fixative composition has been found to be particularly suitable. The mixing process is typically carried out at room temperature, but one skilled in the art could routinely vary the temperature.

The fixative composition of the invention may be used to fix prokaryotic or eukaryotic live cells of any type, and especially bacteria and mammalian cells. The cells are contacted with a suitable amount of the fixative composition, and allowed to remain in such contact for at least about one minute, with about twenty minutes to about two hours of incubation preferable. Temperatures maintained during such incubation are generally 0° C. to about 37° C., with room temperature preferable. Amounts of fixative composition suitably used vary from (relative amounts in volume/ volume of cell sample to fixative composition) about 1:1 to about 1:100 (v/v), with about 1:10 to about 1:30 (v/v) particularly suitable. Excess cell fixative composition may be removed by any conventional means, including centrifugation, and the cells may be resuspended in a suitable cell suspension medium, such as buffer, if desired, prior to cell analysis. One skilled in the art of cellular fixation may routinely vary these aforementioned cell treatment parameters to obtain the desired cell fixation without substantial destruction of cellular properties. In preferred embodiments, the fixative composition of the invention is used in the fixing of bone marrow and blood cells, and especially white blood cells. The cells so fixed may then be examined by any suitable technique known to the art. Examples of such cell analysis would be through the use of a microscope, including an electron microscope, light microscopy, immunofluorescence, flow cytometry, and the like.

A preferred method of cellular analysis utilizing the fixative composition of the invention is through the use of flow cytometry. By way of background, flow cytometers exist in a variety of configurations depending on their intended use. However, they all contain four essential features. Each has a source of incident light, a fluid stream that carries the sample to the point where the incident light is focused, an optical system that converts light reflected off or emitted from the sample into electronic signals, and finally, a means to output the information to the user. Lasers are the most common source of light because they deliver light of a single wavelength at very high intensity. Although flow cytometers have been used on a wide variety of samples, including bacterial cells, chromosomes, tumor cells and others for illustrative purposes, this discussion will emphasize the analysis of a sample comprising a single cell suspension of white blood cells.

In general, to analyze a suspension of cells, the sample is introduced into the center of a fluid stream through a narrow injection port. The stream serves two purposes; first to bring the cells to the point where both the incident light and optical system are focused, and second to orient the cells in single file. Because cells travel in single file, they are interrogated by the light beam one at a time, and the light reflected or emitted by each cell is measured and recorded independent of the other cells in the sample. As a cell is carried into the laser light, it breaks up the beam and scatters it in all directions. Although the cell scatters the light, it does not change the light's wavelength. Therefore, scattered light travels along a different path but maintains the same wavelength as the incident light beam. Typically, the cell suspension has been treated with either fluorescent dyes or antibodies coupled to fluorescent dyes. These fluorescent compounds absorb light of one wavelength and emit light of a longer wavelength. Thus, if the cell contains the fluorescent dye or has reacted with the antibody-dye complex, in addition to scattering light, the cell will emit light of the wavelength characteristic of the fluorescent dye. The amount of light emitted is proportional to the quantity of fluorescent molecules present. The quantity of light emitted by each cell is measured and referred to as its "fluorescence intensity", which is depicted as a numerical value on a scale that is designated by the user, such as 1 to 10,000.

Flow cytometers typically contain several photomultiplier tubes to convert photons into electric impulses. Filters placed in front of each photomultiplier select the wavelength of light to which the photomultiplier will respond. The incident beam is prevented from entering the detection system containing the photomultiplier tubes; therefore, only light scattered by a cell, or emitted from it as fluorescence, is allowed to reach the photomultipliers. Scattered light is collected in two places; at a low angle only slightly deflected from the axis of the incident beam and at a right angle to the beam. The former is called low angle or forward scatter; whereas, the latter is called right angle or side scatter. The reason for measuring scattered light at two different angles is because forward and side scatter provide different information about the cell. How much light is scattered in the forward direction depends on the cells's size and its index of refraction. The bigger the cell the more light it scatters in the forward direction. Light scattered at right angles to the beam is less dependent on cell size than on the complexity and number of intracellular organelles.

Lymphocytes are small cells and therefore have low forward scatter. Lymphocytes also exhibit low side scatter because they have very little cytoplasm and regularly shaped nuclei. Monocytes are larger, their cytoplasm grainier, and their nuclei more complex in shape than lymphocytes. As one would predict, monocytes scatter more light than lymphocytes in both the forward and side directions. Granulocytes may vary in size from being as small as lymphocytes to being larger than monocytes. The broad range of forward scatter exhibited by granulocytes reflects this size heterogeneity. However, because of their cytoplasmic granules and irregular shaped nuclei, granulocytes exhibit the most side scatter of the three main cell types in blood. The light scatter of each cell as it passes through the beam is measured and may be plotted on a graph of forward scatter (FSC) versus side scatter (SSC). Such a plot allows the operator to separate and identify cell types and direct the instrument to display and save data from one, two, or any combination of cell types.

Figure 2:
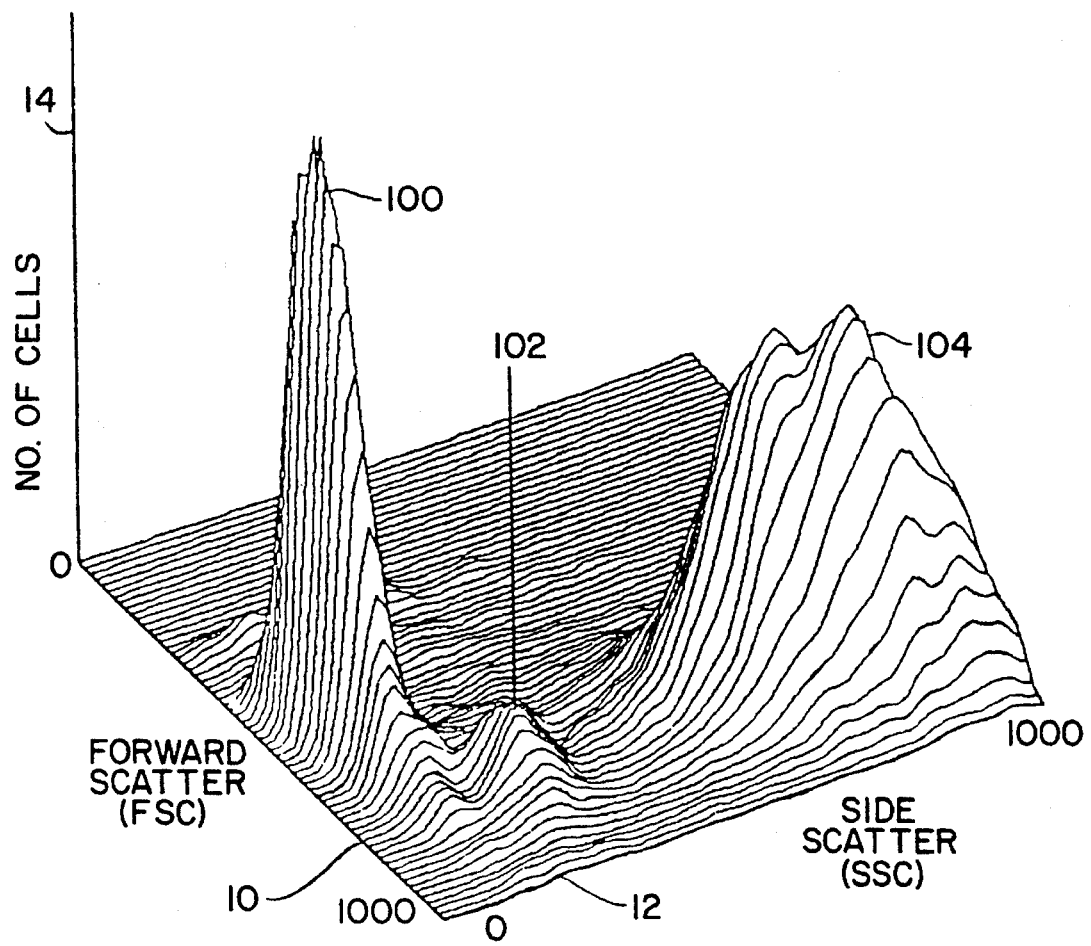
FIG. 2 is a three-dimensional plot obtained with the use of a FACScan flow cytometer demonstrating the distribution of white blood cell clusters in a cell population fixed with the fixative composition of the invention.

The use of light scatter is illustrated in FIGS. 1 and 2, which are three-dimensional representations of the number of cells having light scattering properties as measured on a FACScan flow cytometer available from Becton Dickenson Corporation. Forward light scatter was plotted on the abscissa (X-axis) 10, versus SSC on the ordinate (Y-axis) 12. The number of cells is represented on the Z-axis, 14. The intensity of FSC and SSC for each cell was measured and given a relative value on a scale of 1 to 1000. FIG. 1 shows the results using live unfixed cells, with 100 representing the lymphocyte cluster, 102 representing the monocyte cluster, and 104 representing the granulocyte cluster respectively. FIG. 2 shows the results using cells after having been fixed with the fixative composition of the present invention. Although fixed and made permeable, it was evident that cell clusters remained well defined. Because light scatter depends on factors such as cell size, cytoplasmic complexity and the cell's index of refraction, it was not surprising to find that the light scatter of fixed cells had varied a little from unfixed cells. However, it was surprising to find that after fixation, not only could the three populations of cells be resolved by light scatter alone, but that the separation of lymphocytes, monocytes and granulocytes was improved.

Information that a cell is a lymphocyte, monocyte or granulocyte is useful, but more information than that may be required for a complete analysis. There are many different kinds of lymphocytes and they have quite distinct functions. Some lymphocytes produce antibodies (B-cells), while others serve to regulate the immune system or carry out certain effector functions (T-cells). To be able to identify and enumerate functional subsets of lymphocytes is essential in immunologic research and in diagnosing and monitoring diseases of the immune system. Yet, the functional subsets of lymphocytes cannot be differentiated solely on their light scatter. Fortunately, lymphocytes that differ in function also differ in the antigens they express. As a result, antibodies have been developed that react with specific functional subsets of T-cells. Helper T-cells, for example, are critical to the overall function of the immune system. As their name implies, their role is to help the immune system mount an effective response against foreign substances such as viruses, bacteria and parasites. Helper T-cells express the CD4 molecule on their surface and anti-CD4 antibodies react with these helper T-cells. The flow cytometer can exploit this fact to determine how many of an individual's lymphocytes are of the helper type. A fluorescent molecule is coupled to the anti-CD4 antibody. A commonly used molecule is fluorescein isothiocyanate (FITC). This compound will absorb blue light and emit green light. A sample of white blood cells is reacted with anti-CD4-FITC and then analyzed in the flow cytometer. Cells parading in single file are illuminated by blue laser light and the amount of blue light scattered in the forward and side directions determined. Simultaneously, the amount of green light emitted by the cell is measured. The CD4 positive lymphocytes that reacted with the antibody emit green light in addition to the blue light they scatter. Non-helper T-cells scatter light in a manner identical to helper T-cells, but because no antibody is present they do not emit green light. The flow cytometer can be made to identify a cell as a lymphocyte by virtue of its light scatter profile, and then count the number of lymphocytes that emit green light versus the number that do not. In this way, the proportion of lymphocytes that are helper cells may be determined.

Not every cell that reacts with anti-CD4-FITC is a helper T-cell. Monocytes also express CD4 on their surface, but at a lower concentration than helper T-cells. The lower concentration of CD4 means less antibody binds to monocyte surfaces and so they emit less green light. This makes them dimmer than helper T-cells, but brighter than CD4 negative cells. However, because monocytes have greater forward and side scatter than lymphocytes, the user can direct the flow cytometer to accept or ignore data from cells having the desired light scatter profile. The ability to discriminate light scatter profiles allows the user to get an accurate count of CD4 positive lymphocytes without interference from CD4 positive monocytes. This may be particularly important in some diseases such as Acquired Immunodeficiency Syndrome (AIDS). Helper T-cells may appear less fluorescent or dimmer in AIDS patients than in healthy people. Were it not for the light scatter profile identifying a cell as a lymphocyte, dim CD4 helper T-cells might be otherwise mistaken for monocytes, which could lead to an underestimate of the number of helper T-cells.

Figure 3:
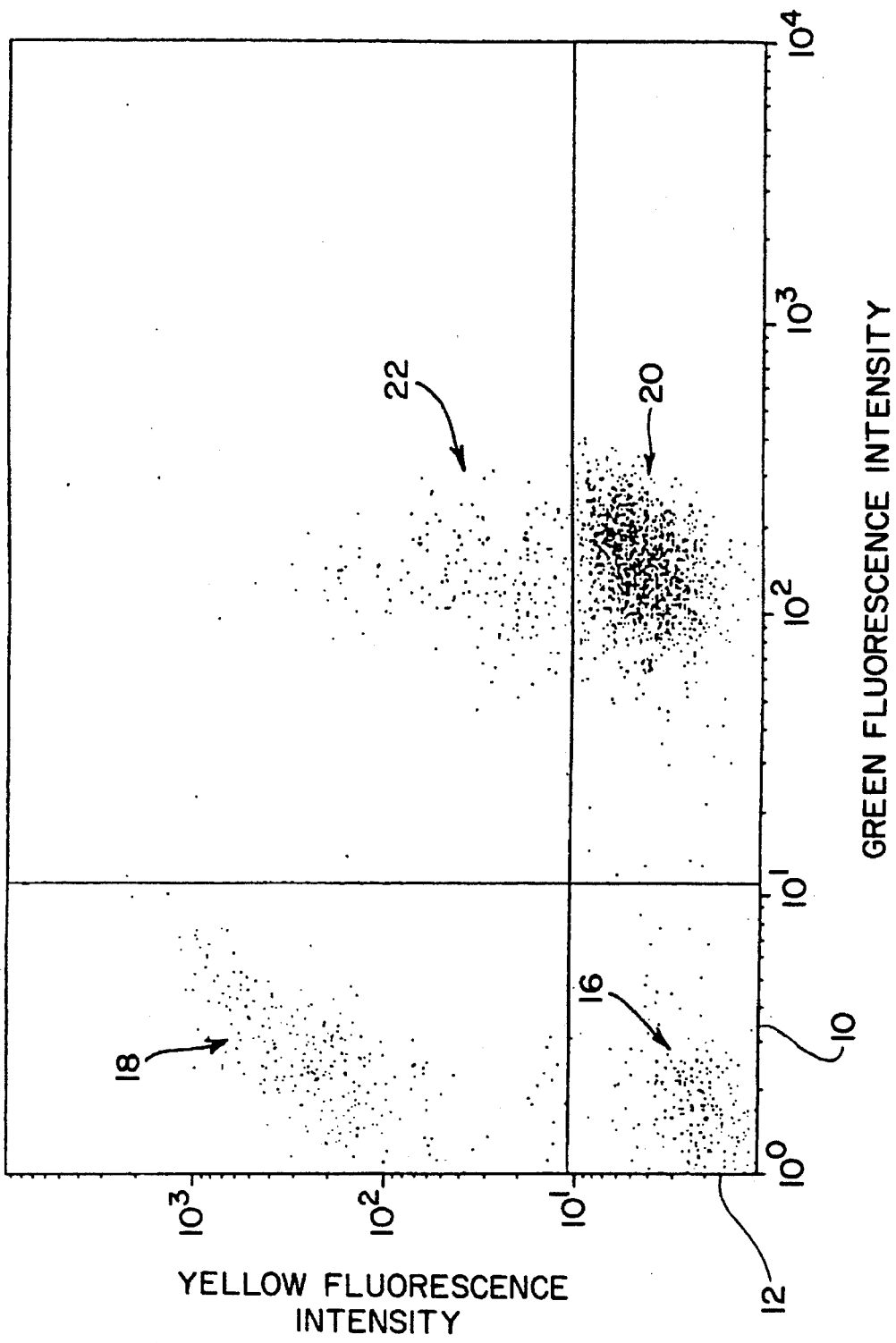
FIG. 3 is a cytogram obtained with the use of a FACScan, demonstrating the results of a double antibody staining assay.

A more complicated assay would employ a second antibody added simultaneously. In this case, the second antibody would have a different specificity from the first, and be coupled with a dye that emits light of a different color. Typically, phycoerythrin (PE) is used for this purpose, because it too absorbs blue light, but fluoresces yellow. In this way, one can determine whether a cell reacts with either the FITC labeled antibody, the PE labeled antibody or both. For example, the antigen known as DR is not expressed on T-cells unless the cells have been activated. In contrast, the DR antigen is expressed on most B-cells. If white blood cells are reacted with anti-CD3-FITC and anti-DR-PE antibodies, all four possible combinations of reactivity would be expected. Some lymphocytes would not react with either antibody and would only scatter light. The non-activated T-cells would react with anti-CD3 antibody and emit only green light. B-cells would react with anti-DR antibody and emit only yellow light. However, activated T-cells would react with both antibodies and emit both green and yellow light. Such a situation is illustrated in FIG. 3, which is a cytogram obtained with the use of the FACScan. Here white cells have been reacted with anti-CD3-FITC and anti-DR-PE and the fluorescence of the lymphocytes, selected as lymphocytes on the basis of their light scatter, has been plotted with each cell's green fluorescence intensity on the abscissa 10, and its yellow fluorescence intensity on the ordinate 12. Unreactive cells cluster at the origin 16. B-cells are displaced vertically, in a cluster 18 distinct from unreactive cells but directly above it. Unactivated T-cells are displaced along the abscissa in a cluster 20 distinct from unreactive cells but directly along side of them. Finally, activated T-cells 22 emit just as much green light as unactivated T-cells because they express the same amount of CD3, but they are also displaced vertically because they co-express the DR antigen, and having reacted with the anti-DR-PE antibody, emit yellow light.

The situation may be made even more complex by the inclusion of a third antibody or a DNA/RNA stain that absorbs blue light and emits red light. This arrangement of reagents is not discussed in detail because it does not illustrate any principles of flow cytometry not already covered by the previous discussion of one and two color reagent analysis; however, it does serve to illustrate how complex and sophisticated flow cytometric analysis of cells may become. By way of example, if the third reagent is a DNA stain, then the amount of DNA in a cell may be measured. The amount of DNA is dependent upon whether the cell is at rest, synthesizing DNA in preparation for cell division, or is about to divide. Quantitating the amount of DNA allows the user to selectively examine cells in various stages of the cell cycle. It then becomes possible to determine whether certain antigens are always expressed by a cell, or only present during restricted portions of the cell cycle. Such data is analyzed essentially as done for one and two color assays, but with greater appreciation for the complexity of simultaneous reactions being measured.

In accordance with the cellular analysis method of the present invention, a cell sample is first obtained from any of a variety of cell sources. Such sample may or may not be purified or otherwise pre-treated in accordance with conventional cell analysis protocols. In the preferred embodiments, a blood sample is obtained. Example II below describes a typical blood sample collection procedure. It should be emphasized, however, that the current method may be carried out without ficolling red blood cells or lysing red blood cells from the whole blood sample prior to fixation (see Example IV). The cellular fixative composition of the invention is mixed with the cells using a quantity of fixative sufficient to fix the cells without substantially destroying their surface membranes.

By way of illustration only, a sample of a patient's whole blood may be obtained by routine venipuncture, drawing the blood sample into a tube containing an anticoagulant such as EDTA or heparin. Approximately 0.1 mls of the whole blood is then mixed with 2 mls of fixative solution prepared in accordance with the teachings herein, and maintained at room temperature. The blood/fixative mixture is incubated for 30 minutes at room temperature, centrifuged to pellet the cells, and the supernatant fluid then removed by aspiration. The cells so fixed are resuspended in wash buffer and allowed to sit for about 10 minutes. The cells are then washed two times in phosphate buffered saline and serum. Optionally, any remaining red blood cells may be lysed using standard lysing procedures.

This basic procedure may be varied in many ways. For example, it may be desirable to first dilute the whole blood sample with an isotonic diluent before proceeding with the fixation method steps. Lysed whole blood may also serve as the sample. The whole blood would be first treated to lyse red blood cells by standard methods and procedures such as by ammonium chloride treatment. The unlysed white blood cells are then washed and resuspended in an isotonic medium, in a concentration that is preferably $1-2\times10^7$ cells/ml, and then treated in accordance with the above procedure. Whole blood samples may also first be treated by standard methods on Ficol-Hypaque, to remove red blood cells and granulocytes. Lymphocytes and monocytes are then suspended at preferably about $1\times10^5$ to about $1\times10^8$ cells/ml, and more preferably about $1-2\times10^7$ cells/ml, and fixed as above. One skilled in the art of blood cell analysis will understand and appreciate these and other conventional techniques for blood sample preparation.

Cell analysis is then conducted in accordance with the previously described techniques and concepts and the following examples, just as though the cells were unfixed, live cells.

Using the fixative composition of the invention, and the techniques of flow cytometry, clinicians may study the viral load infecting a sample of a patient's cell population, for example, white blood cells. In certain preferred embodiments, a study of HIV-infected individuals may be performed using the methods described herein. For example, A. Venet et al. in "Quantitation of Cellular Viral Load: Correlation With CD4 Cell Count", from *Viral Quantitation in HIV Infection,* Ed. J. -M. Andrieu, John Libbey Eurotext, Paris 1991, pp 27–36, describes the usefulness of monitoring viral load. However, he employs the cumbersome, hazardous, and costly techniques of cell culture to attempt to elucidate the required information from various patients' blood cell analyses.

Using techniques of flow cytometry with the resulting data analysis as depicted in FIGS. 1, 2, and 3, and the fixative composition as described herein, a clinician may analyze a patient's blood sample to determine cell phenotypes, which cells are infected with virus, and how many cells are growing the virus. One could even determine "how much" virus is actually in certain cells, in some cases. Using this information, the clinician may then make decisions of diagnosis, therapeutic monitoring, patient prognosis, and the like. For example, two patients having a similar CD4 positive count may demonstrate vastly different clinical presentations and progression. Using the techniques and compositions of the invention, it is possible to determine each patient's respective virus burden. For example, one patient may have a CD4 count of 200, but may demonstrate less than 0.1% CD4 positive cells that are actually replicating virus. The second patient may have 4% of their CD4 positive cells replicating virus. In this latter case, the disease progression may be further along, and the prognosis poorer. Or, the virus may have acquired a drug resistance, and the clinician could decide to change the treatment regimen.

Many viruses may be monitored in a patient's sample for their own sake or simultaneously with the HIV virus or some other virus of interest, in a similar manner. Interestingly, it may be the existence of other viruses, such as hepatitis, that are first detected in an HIV patient who is asymptomatic. Sub-clinical viremia due to one or more other viruses may also indicate that a patient's immune system is breaking down. This may occur before the HIV virus itself becomes rampant. Also, HIV in the presence of an increasing viral burden from other viruses could be a sign of true immunosuppression. Thus, the techniques and compositions as discussed herein provide a rapid overall assessment of the immune system's competence or function.

A test kit containing the fixative composition of the invention in conjunction with suitable cell markers is also provided for the convenience of the researcher and clinician. By way of example, a useful combination reagent kit comprises a vessel containing the fixative composition of the invention, along with vessels containing Orthomune™ OKT4, Orthomune™ OKT8, and Orthomune™ OKDR, which are antibodies available from Ortho Diagnostic Systems Inc., Raritan, N.J. This kit is then utilized in accordance with the techniques herein described to monitor various types of virus infection. The user will understand that this kit is used in conjunction with one or more antibodies to all or a part of the virus of interest. Using such a combination reagent kit, a patient's immune system may be panoramically monitored. In preferred combination kit embodiments, the kit itself may include antibodies or panels of antibodies to various viruses of interest. For example, in the detection of HIV, one or more antibodies to the HIV virus, such as anti-p24, anti-p17, anti-gp41, anti-gp120, and the like are also included in the kit in conjunction with certain antibodies to cellular surface markers such as the aforementioned Orthomune™ OKT antibodies.

The following are more specific embodiments of the present invention but should not be considered limitative thereof.

EXAMPLE 1

Comparison Examples Showing Failure of Current Art to Preserve Light Scatter Properties and Staining of Cell Surface Antigens Comparative Example 1: Cell Population Discrimination After Paraformaldehyde Fixing Four grams of paraformaldehyde (PF) were placed in 400 mls of phosphate buffered saline (PBS). The 1% (wt/v) PF suspension was heated, with constant stirring, until all PF was in solution.

Blood was collected from a single donor into heparinized tubes then centrifuged (457×g, 22° C., 10 minutes). The buffy coat from two blood collection tubes was pooled in a 50 mL centrifuge tube and the total volume adjusted to 35 mLs using Hanks Balanced Salt Solution (Mediatech), supplemented with 5% (v/v) horse serum (HBSP). Ten mLs of ficol-hypaque (Lympho-paque, Nocomed Pharma As) was layered underneath the buffy coat being careful to prevent mixing of the Ficoll-buffy coat interface. The tube was spun at 1170×g for 20 min at 22° C. Peripheral blood lymphocytes and monocytes present at the ficoll interface were collected. The cell pellet containing red blood cells and polymorphonuclear leukocytes was discarded. Lymphocytes and monocytes were diluted in ice cold HBSP then pelleted by centrifugation (457×g, 4° C., 8 minute). Cells were again washed in HBSP.

Cells were washed once in PBS, then resuspended in 4 mLs of PBS ($4\times10^7$ cells/mL). The cells were separated into 4 1 mL aliquots. The first tube received 1 mL of PBS and tubes 2 through 4 received 1 mL of 1% paraformaldehyde. All tubes were incubated for 30 min at room temperature. All tubes were washed twice in PBS. Tubes 1 and 2 were put in ice until needed. Cells in tubes 3 and 4 were resuspended in 1 mL of PBS. To tube 3 was added 1 mL of 0.5% (wt/v) Nonidet P40 (NP40; BDH Limited), and it was incubated 30 minutes at room temperature. To tube 4 was added 6.6 mLs of methanol (−70° C.) and it was incubated 30 minutes at 0° C.

All cells, regardless of treatment, were washed twice in 50 mLs of HBSP plus 2% (v/v) human AB serum (457×g, 4° C., 8 minutes). All cells were resuspended at a concentration of $1\times10^7$ cells/mL in HBSP plus 2% human AB serum (HBSP-AB). 200 uL of each cell suspension was incubated with 20 uL of the fluorescein isothiocyanate (FITC) conjugated monoclonal antibodies: Control, OKT3, OKT4, and OKT11 (Ortho Diagnostic Systems Inc., Raritan, N.J.). Cell suspensions were incubated for 30 minutes at 0° C., then washed twice by centrifugation (457×g, 4° C., 8 minutes) in ice cold HBSP-AB. Each suspension was resuspended in 0.5 mL of HBSP-AB.

The light scatter properties and level of fluorescent antibody binding was determined through routine flow cytometric techniques using a FACScan (Beeton Dickinson) flow cytometer. The FACScan was equipped with an argon laser emitting light at 488 nM. Fluorescence detector 1 (FL1) equipped with a 530/30 nM band pass filter was used for quantitating FITC fluorescence. Unless otherwise indicated light scatter measurements were made on a linear scale of from 0–256 units and fluorescence was measured on a logarithmic scale of 1 to $10^4$ units.

Forward light scatter (FSC) and the level of FITC fluorescence for unfixed live cells treated with a Control-FITC antibody was measured. Cells pre-treated with 1% paraformaldehyde (PF) were also analyzed in the same manner.

Although the cells had been treated with 1% PF, two distinct cell populations were discriminated by FSC. Lymphocytes were seen with a FSC around 105 (on a scale of 1 to 256) whereas monocytes had a FSC around 180. Cells treated with 1% PF displayed more nonspecific binding of control-FITC antibody than did live, unfixed cells.

Experiments were also conducted wherein cells were treated with OKT3 antibody and measured in a similar manner. OKT3 reacts with the molecule CD3 on the surface of T cells. CD3 is not present on B cells or monocytes, so these cells fail to react with OKT3.

Lymphocytes that bind OKT3 were evident in the PF treated cells. The average fluorescence of PF treated cells was lower than untreated cells; and the positive and negative populations were not as well separated following PF treatment. The lower binding intensity of OKT3 suggests CD3 may have been damaged by PF treatment, but not altered to the point where OKT3 will no longer bind. Additional evidence that lymphocytes and monocytes were distinguished on the basis of their FSC was the finding that no CD3 positive T cells were present in the monocyte cell cluster (FSC approx. 180 on a scale of 1–256).

Cells were also treated with the antibody OKT4. OKT4 binds to CD4 on the surface of the helper subset of T cells. OKT4 bound to the PF treated lymphocytes. Unlike CD3, CD4 is expressed at a low level on the surface of monocytes. Thus, live, unfixed monocytes showed dim fluorescence with OKT4. PF treated monocytes did not appear to bind OKT4. However, because CD4 is expressed at low levels on monocytes, even a small amount of damage to CD4 would render these cells negative. As was the case with CD3, CD4 does appear to have been damaged by PF treatment, but not destroyed.

OKT11 staining was also performed and measurements taken in the same manner as before. OKT11 binds CD2 on the surface of T cells. On live unfixed cells, the OKT11 positive population displayed only modest fluorescence. No OKT11 staining was observed on PF treated cells. Treatment of cells with PF appears to have altered CD2 in a way that prevents OKT11 from binding to its epitope.

Comparative Experiment 2: Methanol Permeation

In order to visualize intracellular antigens, it is not enough to simply fix cells. Cells must also be made permeable to molecules as large as antibodies. The methods most frequently employed to permeabilize cells are methanol or detergent treatment of fixed cells (reviewed in Jacobberger, J. W., (1989) Cell cycle expression of nuclear proteins. In A. Yen (ed.), Flow cytometry: advanced research and clinical applications. CRC Press, Inc. Boca Raton Fla.). Methanol further fixes proteins, randomizes their conformation and extracts membrane lipids. Detergent treatment extracts membrane lipids, creating holes where antibodies may pass freely in and out of the cell.

Immunostaining and light scatter properties of cells fixed in 1% PF versus cells fixed in 1% PF followed by methanol permeabilization was measured. The ability to discriminate lymphocytes from monocytes on the basis of their FSC is diminished by methanol treatment. In addition, methanol treated cells had increased nonspecific binding of control-FITC antibody. The most important finding, however, was that methanol treated cells no longer reacted with OKT3, OKT4, and still did not react with OKT11.

Comparative Example 3: Detergent Treatment

Immunostaining and light scatter properties of cells fixed in 1% PF versus cells fixed 1% PF followed by detergent treatment (0.5% NP40) was also measured for comparison purposes. The ability to discriminate lymphocytes from monocytes was diminished by detergent treatment. Detergent treated cells also showed a marked increase in nonspecific control-FITC binding over cells treated with 1% PF. OKT3 did bind detergent treated cells, however, there was very little separation between the positive and negative populations. Poor FSC separation of lymphocytes and monocytes made it unreliable to separate these populations by light scatter. As a result, the percent OKT3 positive lymphocytes could not be determined accurately following detergent treatment. Even though OKT3 still bound CD3 positive lymphocytes, it could not be known with certainty how many of the CD3 negative cells were truly lymphocytes and how many were monocytes with FSC altered by detergent treatment. The effect of detergent treatment on monocyte light scatter properties became evident when detergent treated cells were treated with OKT4. OKT4 bound lymphocytes, and to a lesser extent monocytes, as expected since both contain CD4 positive cells. Three populations of cells, and their OKT4 binding, were measured successfully. The three populations that were determined were CD4 negative lymphocytes with no OKT4 binding, monocytes having a low density of CD4 with intermediate staining, and CD4 positive lymphocytes with bright fluorescence. However, in the detergent treated cells, many monocytes had light scatter values between 80 and 140 PSC; the same range of FSC values obtained for lymphocytes. It was clear from this result that following detergent treatment, the lymphocyte light scatter cluster was heavily contaminated with monocytes.

EXAMPLE 2

Preservation of Cellular Antigenic Specificities Following Fixation With the Composition of the Invention The fixative reagent was prepared by adding constituents to distilled $H_2O$ to final concentrations: 14% (v/v) dimethyl sulfoxide (DMSO, Sigma Chemical Co.); 0.14% (w/v) polyoxyethylene sorbitan monolaurate (Tween 20, Aldrich Chemical Company); 39.2 mM 2,4-dinitrobenzene sulfonic acid sodium salt (DNBS, Aldrich Chemical Co.); 1.51% formaldehyde (Ultrapure 10% EM grade, Polysciences Inc.); 1.470 mM $KH_2PO_4$; 2.683 mM KCl; 8.058 mM $Na_2HPO_4$ and 67 mM NaCl. The pH of the fixative solution was adjusted to 7.4; and the solution was stored in an amber bottle overnight at room temperature.

Blood was collected by venipuncture directly into a tube containing K3-EDTA as the anticoagulant. The blood and anticoagulant was mixed and kept at room temperature until needed (approximately one hour).

Ten mLs of whole blood were placed in a 50 mL centrifuge tube. Whole blood was diluted with 40 mLs of freshly prepared buffered ammonium chloride lysing reagent (Ortho Diagnostic Systems Inc.). Blood Was incubated 20 minutes at room temperature with occasional mixing. White blood cells were pelleted by centrifugation (457×g, 21° C., 8 minutes). White blood cells were washed twice by centrifugation (457×g, 21° C., 8 minutes) in phosphate buffered saline (PBS) at room temperature. Washed cells were resuspended in PBS at a concentration of $2 \times 10^7$ cells/mL. The pool of white cells was separated into aliquots. Cells that were not to be fixed were diluted with an equal volume of PBS+5% (v/v) horse serum (PBS/S) and placed on ice until needed. The cells to be fixed were diluted with an equal volume of fixative reagent. Cells were mixed and incubated for 30 minutes at room temperature. After 30 minutes, fixed cells were washed twice in 50 mLs of PBS. Live and fixed cells were washed once in "Block Solution." Block solution was composed of 25% (v/v) goat serum+5% (v/v) horse serum +5% (w/v) bovine serum albumin (BSA). Live cells were resuspended to $2 \times 10^7$ cells/mL in block solution and placed on ice for one hour. Fixed cells were also resuspended in block solution at $2 \times 10^7$ cells/mL, but kept at room temperature for one hour.

DIRECT IMMUNOSTAIN

Cell surface antigenic determinates were stained using antibodies to cell surface markers, conjugated directly to FITC (OK-control, OKT3, OKT4, OKT11 and OKT3/OKDR-PE combination, all available from Ortho Diagnostic Systems Inc., Raritan, N.J.). 100 uL of either live or fixed cell suspension was placed in a reaction tube and 10 uL of the appropriate antibody or control added to the tube. Cells and antibody were incubated for 60 minutes. All incubations and washes using live cells were done at 0° C., whereas all incubations and washes using fixed cells were done at room temperature. After 60 minutes, cells were washed three times in PBS/S using 2 mL per wash. After the last wash, cells were resuspended in 0.5 mL of PBS/S and analyzed on a FACScan flow cytometer.

INDIRECT IMMUNOSTAIN

To determine whether fixation had made cells permeable to antibody while retaining their cytoplasmic antigens, live and fixed cells were reacted with mouse monoclonal antibodies specific for the cytoplasmic proteins gelsolin and vimentin. Anti-gelsolin (clone No. GS-2C4, Sigma Chemical Co.) and anti-vimentin (clone No. V9, Sigma Chemical Co.) were not conjugated to fluorescent dyes. Therefore, binding of these antibodies could not be determined "directly." Instead, binding of these antibodies to cells was determined "indirectly" by reacting treated cells with goat anti-mouse IgG-FITC. Immunostaining of cytoplasmic antigens was done by adding 10 uL of Control IgG2a mouse antibody (10 ug/mL), or 10 uL of anti-gelsolin (diluted 1/100 in block solution) or 10 ul of anti-vimentin (diluted 1/60 in block solution) to 100 ul of fixed or live cell suspension. Cells and antibody were incubated for one hour as described above, then washed three times in PBS/S using 2 mLs per wash. After the last wash, the supernatant fluid was removed by aspiration, and the cells resuspended in 100 uL of block solution. Each suspension then received 200 uL of goat anti-mouse IgG-FITC conjugate (F(ab')$_2$, Sigma Chemical Co.) diluted 1/75 in block solution. Cells were again incubated for 60 minutes, then washed three times in PBS/S, using 2 mL per wash. After the last wash, cells were resuspended in 0.5 mL of PBS/S and analyzed on a FACScan flow cytometer.

It is known in the art that fixed cells usually exhibit a substantial increase in either autofluorescence, nonspecific binding of antibody, or both. It is also known, the amount of nonspecific binding by antibody can be minimized with appropriate blocking reagents and cell washing conditions. In this example, all cells were treated with a blocking solution and washed in the same wash buffer.

In the interest of conserving space, time and avoiding undue repetition, only data from the lymphocyte cluster is discussed herein. The lymphocyte cluster was identified by FSC versus SSC and a "gate" or region was established to narrow the output of the computer analysis to those cells within the defined region or "lymphocyte gate." Although only the lymphocyte analysis is discussed, fixed lymphocytes were representative of how fixed monocytes and granulocytes react with anti-gelsolin, anti-vimentin, and antibodies against cell surface markers appropriate to their respective cell types.

OK-Control-FITC is a mouse IgG2a antibody that does not react with any known cellular antigens. Therefore, any green fluorescence emitted by cells following treatment with this antibody is due to nonspecific binding of antibody to cells. The nonspecific binding by live and fixed cells was determined. When reacted with OK-Control, 100% of live cells had a fluorescence intensity less than 3.92 (on a scale of 1 to $10^4$), with a mean intensity for live cells of 1.20. Nonspecific binding of antibody to fixed cells was only slightly higher than that of live cells. 99.5% of fixed cells had fluorescence less than 13.82, with a mean fluorescence intensity of 3.99. The data therefore demonstrated that cells fixed and stained by the present reagent and methods do not bind significant quantities of antibodies nonspecifically.

Staining of the cell surface molecule CD3 by OKT3-FITC antibody was measured. 77.4% of live lymphocytes were positive for CD3, compared to 77.9% of the fixed lymphocytes. The mean fluorescence intensity for CD3 positive live cells was 188.83. The mean fluorescence intensity of CD3 positive fixed cells was 144.68; 23% lower than the intensity of live cells. Although the intensity of staining was modestly lower, the reagent and methods as described herein did not destroy the ability of OKT3 to bind CD3 on fixed cells; and enough OKT3 was bound by fixed cells that CD3 positive lymphocytes could be separated unequivocally from CD3 negative lymphocytes, based on their fluorescence intensity. This result is in marked contrast to cells fixed and made permeable by paraformaldehyde and methanol treatment as performed in the art, where the ability of OKT3 to bind CD3 had been destroyed completely (see Comparative Experiment 2 above).

Staining of the cell surface molecule CD4 by OKT4-FITC antibody was also performed. 55.1% of live lymphocytes were positive for CD4, compared to 52.7% of the fixed lymphocytes. The mean fluorescence intensity for CD4 positive live cells was 69.57. The mean fluorescence intensity of CD4 positive fixed cells was 63.74; 8% lower than the intensity of live cells. Although the intensity of staining was modestly lower, the present invention's reagent and methods did not destroy the ability of OKT4 to bind CD4 on fixed cells; and enough OKT4 was bound by fixed cells that CD4 positive lymphocytes could be separated unequivocally from CD4 negative lymphocytes based on their fluorescence intensity. This result is in marked contrast to cells fixed and made permeable by paraformaldehyde and methanol treatment, where the ability of OKT4 to bind CD4 had been destroyed completely (see Comparative Experiment 2 above).

Staining of the cell surface molecule CD2 by OKT11-FITC antibody was also performed. 85.3% of live lymphocytes were positive for CD2, compared to 84.3% of the fixed lymphocytes. The mean fluorescence intensity for CD2 positive live cells was 49.95. The mean fluorescence intensity of CD2 positive fixed cells was 41.00; 18% lower than the intensity of live cells. Although the intensity of staining was modestly lower, the present invention's reagent and methods did not destroy the ability of OKT11 to bind CD2 on fixed cells; and enough OKT11 was bound by fixed cells that CD2 positive lymphocytes could be separated unequivocally from CD2 negative lymphocytes based on their fluorescence intensity. This result is in marked contrast to cells fixed and made permeable by paraformaldehyde and methanol treatment, where the ability of OKT11 to bind CD2 had been destroyed completely (see Comparative Experiment 2 above). In addition, when lymphocytes were treated with paraformaldehyde followed by NP40 solubilization of membranes, some CD3 and CD4 staining was observed, but no staining of CD2 by OKT11 was seen.

Cells were also incubated with two antibody specificities conjugated to fluorescent molecules having different emission spectra. Cells were incubated with OKT3-FITC and OKDR-PE simultaneously. Dot blot cytograms were obtained from the FACScan where staining of the cell surface molecule CD3 by OKT3-FITC antibody was displayed on the X-axis and staining of the cell surface molecule DR by OKDR-PE was displayed on the Y-axis. The dot plots, which were analogous to that shown in FIG. 3, were divided into 4 quadrants; upper left (UL), upper right (UR), lower left (LL) and lower right (LR). 78.7% (UR+LR) of live lymphocytes were positive for CD3, compared to 79.7% of the fixed lymphocytes. B-cells represented 6.8% of the lymphocyte population as determined by OKDR staining (upper left) of live cells. For fixed cells, B-cells represented 7.4% of the lymphocytes, in good agreement with the live cell population. There was also excellent agreement between the live and fixed cell populations on the percentage of activated T-cells, as determined by co-expression of the DR and CD3 antigens. 4.48% (upper right) of the live T-cells and 4.22% of the fixed T-cells were determined to have been activated. These results not only extend the list of cell surface antigens that may be detected post-fixation to include DR, but also serve to demonstrate that multiple antigenic specificities may be probed simultaneously when cells have been fixed using the reagents and methods as described herein.

Staining of intracellular antigens was done using an indirect immunostain procedure, as described above. Because of this, OK-Control-FITC was not the appropriate negative control. Instead, cells were incubated with an unconjugated control IgG2a antibody, washed and incubated with the goat anti-mouse-IgG-FITC. 99.6% of live cells had a fluorescence of 3.92 or less, with a mean fluorescence of 1.21. 99.4% of fixed cells had a fluorescence of 12.86 or less, with a mean fluorescence of 5.84. As was seen with the direct antibody conjugate control, the data demonstrate that cells fixed and stained by the present reagent and methods do not bind significant quantities of antibodies nonspecifically.

Staining of the cytoplasmic molecule gelsolin by anti-gelsolin antibody demonstrated that 0.4% of live lymphocytes were positive for anti-gelsolin fluorescence, compared to 91.4% of the fixed lymphocytes. The mean fluorescence intensity of the anti-gelsolin negative live cells was 1.22. The mean fluorescence intensity of anti-gelsolin positive fixed cells was 50.45. Gelsolin is a cytoplasmic antigen not expressed on the cell surface. As a result, live cells didn't stain positive for gelsolin because antibody could not enter the cell. In contrast, the interior of the cell was accessible to antibody when cells were fixed by the reagent and methods of the present invention. Anti-gelsolin was a whole IgG molecule, not a fragment; therefore, molecules at least as large as 150,000 daltons could freely enter and leave these fixed cells.

Staining of the cytoplasmic molecule vimentin by anti-vimentin antibody demonstrated that 0.6% of live lymphocytes were positive for anti-vimentin fluorescence, compared to 92.0% of the fixed lymphocytes. The mean fluorescence intensity of the anti-vimentin negative live cells was 1.24. The mean fluorescence intensity of anti-vimentin positive fixed cells was 555.01. Vimentin is a cytoplasmic antigen not expressed on the cell surface. As a result, live cells didn't stain positive for vimentin because antibody could not enter the cell. In contrast, the interior of the cell was accessible to antibody when cells were fixed by the reagent and methods of the invention. It is important to note that vimentin has a molecular weight of 58,000 daltons, whereas anti-vimentin has a molecular weight of 150,000 daltons. Therefore, these results show that during fixation, small cytoplasmic proteins are retained by the cell and held in place, despite the cell having been made permeable to molecules the size of intact antibodies.

It has been seen that cells fixed by the reagent and methods of the present invention maintain sufficient light scatter properties to allow lymphocytes, monocytes and granulocytes to be discriminated, one from the other. Fixed cells allow free access of antibodies to internal cellular antigens, yet these same antigens have been fixed in place and are not washed out of the cells, even though the antigen may be smaller than an antibody molecule. Finally, cell surface molecules on fixed cells are intact and may be immunostained by one or more antibody molecules, providing for identification and quantification of white blood cell functional subtypes.

EXAMPLE 3

Effect of Fixative Composition on Immunostaining of Cytoplasmic Antigens

Investigation Using Computer Aided Statistical Design and Analysis—("SEDA")

In order to examine the effect of the fixative composition on cytoplasmic antigen staining, a human cell line was used in place of white blood cells. A cell line was used because the expression of cytoplasmic antigens would be homogeneous. Therefore, differences in the percentage of cells scored positive, or the fluorescence intensity of individual antigens, could be attributed to differences in the composition of the fixative rather than differences in antigen expression by heterogeneous cell types.

T-cells express CD3 on their cell surface. However, some T-cell tissue culture lines express cytoplasmic CD3 but little or no cell surface CD3 (Van Dongen et. al. Blood, 71: 603, 1988). The CEM T-cell line is one such cell line; having cytoplasmic but no cell surface CD3. CEM cells were gown, fixed with a variety of fixative formulations, then reacted with anti-CD3 (OKT3), anti-gelsolin and anti-vimentin.

The fixative reagent of the invention was prepared by adding constituents to distilled $H_2O$ to final concentrations as called for by the computer aided statistical experimental design (see Table E3-1). The fixative formulations were prepared the day before the experiment and stored overnight in the dark and at room temperature. Regardless of the fixative being tested, the method of fixation was as follows: CEM cells were pelleted (457×g, 21° C., 8 minutes), then washed twice by centrifugation (457×g, 21° C., 8 minutes) in PBS/S at room temperature. Washed cells were resuspended in PBS/S at a concentration of $2.5 \times 10^6$ cells/mL. The pool of cells was separated into 1 mL aliquots, then diluted with an equal volume of the appropriate fixative reagent. Cells were mixed and incubated for 30 minutes at room temperature. After 30 minutes, fixed cells were washed twice with 10 mLs of ice cold PBS. All cells were washed once more in PBS/S then resuspended to a concentration of $3.3 \times 10^6$ cells/mL.

Indirect Immunostain

Cells were reacted with OKT3 and the mouse monoclonal antibodies anti-gelsolin (clone No. GS-2C4, Sigma Chemical Co.) and anti-vimentin (clone No. V9, Sigma Chemical Co.). Immunostaining of cytoplasmic antigens was done by adding 5 uL of Control IgG2a mouse antibody (15 ug/mL), or 5 uL of OKT3, or 5 uL of anti-gelsolin (diluted 1/40 in PBS/S) or 5 ul of anti-vimentin (diluted 1/30 in PBS/S) to 100 ul of fixed or live cell suspension. Cells and antibody were incubated for one hour at 0° C., then washed twice in PBS/S using 2 mLs per wash. After the last wash, the supernatant fluid was removed by aspiration, and the cells resuspended in 250 uL of goat anti-mouse IgG-FITC conjugate (F(ab')$_2$, Sigma Chemical Co.) diluted 1/75 in PBS/S. Cells were again incubated on ice for 60 minutes, then washed three times in PBS/S, using 2 mL. per wash. After the last wash, cells were resuspended in 0.5 EL of PBS/S and analyzed on a FACScan flow cytometer.

Statistical Experimental Design and Analysis (SEDA)

Computer aided SEDA was used to further optimize the present invention. Using SEDA, more information could be obtained from a given set of experiments than could be obtained using more traditional methods.

The theoretical basis of SEDA was developed in 1960 by G. E. P. Box and D. W. Behnken. [Box, G. E. P., and D. W. Behnken (1960). Some new three level designs for the study of quantitative variables. Technometrics 2: 455–475.] Although main frame computers used to be required in order to make use of SEDA, it is now available commercially as a PC compatible software package. The software package used in these studies was "X-Stat Statistical Experimental Design/Data Analysis/Nonlinear Optimization"; available through Softpower Incorporated, John Wiley & Sons, Inc.

The essence of SEDA represents a departure from "traditional" experimental design. In a "traditional" experiment, the researcher first identifies all important mechanisms that may impact the result. Then a list is made of important variables to study and the performance parameters to be measured. For a problem as complex as cellular fixation, the list of variables and measured outcomes are long. Thus, a comprehensive optimization of the various parameters is better accomplished by the use of SEDA. For example, if three variables are to be studied, a traditional design would call for two variables to be held constant while the third is varied. If a linear relationship exists between the variables, and the variables are entirely independent, then to be able to predict performance, measurements need to be made at only two points for each variable. However, if the relationship between variables is not linear, the variables interact with each other or their relationship is not known, then each variable must be evaluated at a minimum of three points. Only if there are three points for each variable is it possible to determine if a linear or non-linear relationship exists. To test 3 variables at three levels requires 27 separate combinations. This approach is called a "full three level factorial design". The number of combinations in a full three level factorial design increases exponentially as the number of variables increase. With 4 variables, 81 combinations are required and 5 variables requires 243 combinations. As a result, researchers typically restrict the scope of a study to a manageable number of variables. Unfortunately, when only some of the variables are studied, the final result is determined fundamentally by whether the researcher chose wisely when deciding on the variables to study.

SEDA provides the researcher with the ability to study many more variables simultaneously by reducing the number of combinations required within the experiment. In the example of the experiment having 3 variables, the 3 variables may be called X, Y and Z. The range of values from low to high for X, Y and Z within the experiment may be thought of as defining the dimensions of a cube; with X representing the width, Y the height and Z the depth. A full three level factorial design would require a test at each corner of the cube and all midpoints (27 experiments in all). The Box-Behnken design requires testing only the combinations that represent the mid-point of each edge of the cube, and triplicate determinations of the combination that represents the center of the cube. This reduces the number of combinations from 27 to 15. The advantage of the Box-Behnken design becomes dramatic as the numbers of variables increase. A Box-Behnken design requires only 27 combinations for 4 variable and 46 for 5 variables; compared to 81 and 243 respectively for a three level factorial design. In addition, after the data has been collected and the computer selects mathematical models that correspond to the observed experimental results, SEDA can be used to predict the performance of the assay at any point on the surface or within the volume of the cube.

Experiments were designed using SEDA. A file was created where the variables to be studied (eg. formaldehyde, DNBS, DMSO and detergent concentrations) and the performance to be measured is., staining of cytoplasmic or surface antigen) were entered into the computer. After specifying the upper and lower limit for each variable, the software determined the concentration of each variable for each "run" within the experiment (see Table E3-1). The runs were then put in random order. After the laboratory portion of the experiment was completed, the measured performances corresponding to each run were entered into the computer. The computer determined those variables that had the greatest effect on performance, those that had no effect, and those that interacted synergistically. Regression lines were fitted to the experimental data using linear, interactive and quadratic equations. The mathematical model giving the best fit to the data was chosen and carefully checked for how well it predicted the experimental results.

The computer model could be used to predict assay performance at any concentration or any combination of concentrations within the range of each variable tested. With this capability, countless combinations of reagent concentrations were tested by computer simulation. The ability of these simulated fixative formulations to allow staining of cytoplasmic antigens, or in some cases the degree of harm done to cell surface antigen staining, was predicted. Furthermore, minimum performance criteria were set and an algorithm in the software used to calculate the optimum combination of reagent concentrations to achieve any given desired performance. Once optimized, the computer was instructed to hold all variables at their optimal level except one. One variable was then varied over its entire range and its effect on performance plotted.

Staining of all three cytoplasmic antigens was observed at all concentrations of reagents tested; however, computer analysis of the observed experimental results predicted a preferred embodiment comprising 0.756% formaldehyde, 25.4 mM DNBS, 6.92% DMSO and 0.086% Tween 20 detergent. This computer predicted preferred embodiment was extremely similar to a preferred embodiment illicited through laboratory fixation experiments, wherein the concentrations of the relative components are 0.85% formaldehyde, 30 mM DNBS, 6.9% DMSO and 0.095% Tween 20 detergent. The latter fixative composition was tested on whole blood, whereas the computer modeling was based on the CEM cell line. The concentration of each reagent corresponding to the preferred embodiment was entered into the computer model. A computer generated plot of how formaldehyde concentration effects the fluorescence intensity of cytoplasmic CD3 staining by OKT3 demonstrated that fluorescence intensity declines rapidly as the formaldehyde concentration increases beyond 0.80%, even if all other constituents of the fixative remain at their optimal concentration. Other plots demonstrated the effect of the three other active ingredients in the fixative. It is important to note that the X and Y axes of each graph are different. The Y axis of the formaldehyde plot covers a mean fluorescence intensity range of 50 units, whereas the Y axis on the detergent plot covers a range of 400 units. Over the concentration ranges tested, detergent had the biggest effect on detection of cytoplasmic CD3; followed by DMSO, DNBS and formaldehyde. Detergent, DMSO and DNBS all served to improve CD3 detection in CEM cells. Formaldehyde had adverse effects on CD3 detection at concentrations greater than 0.80%.

Computer analysis of the factors influencing cytoplasmic staining of gelsolin was also performed. Gelsolin detection was insensitive to the concentration of formaldehyde tested in this experiment. A modest increase was predicted with increasing formaldehyde concentration, but the predicted increase was within experimental error. The same may be said of DNBS. Therefore, across the range of DNBS concentrations tested, DNBS was found to have little effect on detection of gelsolin in CEM cells. The concentration of DMSO had the biggest positive effects increasing the mean fluorescence an estimated 160 units. Detergent concentration increased fluorescence an estimated 110 units.

Computer analysis of the factors influencing cytoplasmic staining of vimentin was also performed. Vimentin detection was very sensitive to formaldehyde concentration. A decrease in mean fluorescence intensity of an estimated 250 units was found. Concentrations of DNBS greater than 25 mM was estimated to increase mean fluorescence by as much as 200 units. DMSO also improved the detection of vimentin, increasing mean fluorescence an estimated 150 units. Increasing the DMSO concentration above 4.5% did not appear to help or hurt vimentin detection significantly in CEM cells. Detergent concentration had the biggest effect. An increase in mean fluorescence of 400 units was estimate as the detergent concentration was increased from 0.04% to approximately 0.08%. Higher concentrations were not predicted to improve vimentin detection.

The predictions of the computer model were verified for peripheral blood lymphocytes. White blood cells from a healthy donor were either washed in PBS/S or fixed at final reagent concentrations of 0.755% formaldehyde, 7% DMSO, 0.08% Tween 20 and either 0, 19.6 or 38 mM DNBS. All cells were fixed for 30 minutes at room temperature, then washed. All red blood cells from either fixed or live cell populations were removed by ammonium chloride lysis. The white blood cells were then immunostained using an indirect immunostain procedure and the antibodies anti-gelsolin and anti-vimentin, as described above.

The effect of fixation on the ability to detect cytoplasmic gelsolin and vimentin in peripheral blood lymphocytes is shown in Table E3-2. Less than 0.5% of live cells were stained with anti-gelsolin or anti-vimentin. However, 80 to 90% of fixed lymphocytes stained positive for these antigens. The concentration of DNBS during fixation did not effect the percentage of cells that bound either anti-gelsolin or anti-vimentin. Although the level of fluorescence for anti-gelsolin and anti-vimentin was much lower in this experiment than it was for the CEM cells, there was good agreement with the predictions of the computer simulation. DNBS had little or no effect on the retention and detection of gelsolin, but improved the detection of vimentin. How fixation in the presence of DNBS increases the mean fluorescence of anti-vimentin reactive cells is not known. Because the anti-vimentin was a monoclonal antibody, it is not due to an unmasking of epitopes by DNBS that leads to the binding of other antibody specificities. Instead, this result suggests DNBS may improve access to vimentin in regions of the cell not accessible to antibodies when DNBS is not present during fixation, or that DNBS increases the amount of vimentin retained within fixed cell. Whether it is improved access of antibodies or improved retention of antigen, these results confirmed the added benefit of fixation in the presence of DNBS for some antigens and extended the validity of the computer model to include the behavior of these antigens in peripheral blood cells.

These results show that the combination of active ingredients of the present invention that most improved fixation and detection for each individual antigen could not be predicted in advance. Each individual active ingredient did not influence all antigens in the same way. Detection of gelsolin was most improved by increasing the DMSO concentration; whereas, detection of cytoplasmic CD3 and vimentin was most improved by increasing the detergent concentration. Vimentin and cytoplasmic CD3 detection was improved by increasing the concentration of DNBS, but gelsolin detection was not influenced significantly by DNBS. It is reasonable to speculate, based on these results, that there will be other antigens, either cytoplasmic or cell surface, the fixation of which will be more strongly influenced by certain of the active ingredients over others. However, it remains impossible to anticipate whether an antigen will be preserved or destroyed after having been fixed. It is also impossible to anticipate which of the active ingredients will be the dominant ingredient for preserving antigenic structure after fixation. This data further establishes that although staining of cytoplasmic antigens takes place even in the absence or at low concentrations of the various ingredients, immunostaining is improved in many cases by the use of the DNBS and increasing the concentration of one or more of the other active ingredients.

TABLE E3-1

COMPUTER GENERATED STATISTICAL EXPERIMENTAL DESIGN.

| RUN NUMBER | PERCENT FORM- ALDEHYDE | MILLI- MOLES DNBS | PER- CENT DMSO | PERCENT DETERGENT |
|---|---|---|---|---|
| 1 | 0.70 | 38.0 | 4.5 | 0.07 |
| 2 | 1.00 | 25.0 | 4.5 | 0.10 |
| 3 | 0.85 | 25.0 | 4.5 | 0.07 |
| 4 | 0.85 | 25.0 | 1.0 | 0.04 |
| 5 | 0.85 | 38.0 | 4.5 | 0.10 |
| 6 | 0.85 | 25.0 | 4.5 | 0.07 |
| 7 | 0.70 | 25.0 | 1.0 | 0.07 |
| 8 | 0.85 | 25.0 | 8.0 | 0.10 |
| 9 | 0.70 | 12.0 | 4.5 | 0.07 |
| 10 | 0.85 | 38.0 | 8.0 | 0.07 |
| 11 | 0.70 | 25.0 | 8.0 | 0.07 |
| 12 | 0.70 | 25.0 | 4.5 | 0.10 |
| 13 | 0.85 | 38.0 | 1.0 | 0.07 |
| 14 | 0.70 | 25.0 | 4.5 | 0.04 |
| 15 | 0.85 | 12.0 | 4.5 | 0.10 |
| 16 | 0.85 | 25.0 | 1.0 | 0.10 |
| 17 | 1.00 | 25.0 | 1.0 | 0.07 |
| 18 | 0.85 | 12.0 | 1.0 | 0.07 |
| 19 | 0.85 | 12.0 | 8.0 | 0.07 |
| 20 | 1.00 | 12.0 | 4.5 | 0.07 |
| 21 | 1.00 | 25.0 | 4.5 | 0.04 |
| 22 | 0.85 | 12.0 | 4.5 | 0.04 |
| 23 | 0.85 | 25.0 | 4.5 | 0.07 |
| 24 | 1.00 | 25.0 | 8.0 | 0.07 |
| 25 | 0.85 | 25.0 | 8.0 | 0.04 |
| 26 | 0.85 | 38.0 | 4.5 | 0.04 |
| 27 | 1.00 | 38.0 | 4.5 | 0.07 |

TABLE E3-2

EFFECT OF DNBS CONCENTRATION DURING FIXATION ON DETECTION OF CYTOPLASMIC ANTIGENS IN LYMPHOCYTES.

| ANTIBODY | LIVE CELLS | LYMPHOCYTES FIXED USING | | |
|---|---|---|---|---|
| | | NO DNBS | 19.6 mM DNBS | 38.0 mM DNBS |
| Percent Positive: | | | | |
| Anti-gelsolin | 0.45 | 81.31 | 81.55 | 84.30 |
| Anti-vimentin | 0.31 | 89.66 | 86.82 | 90.17 |
| Mean Fluorescence: | | | | |
| Anti-gelsolin | NA | 18.91 | 20.24 | 21.82 |
| Anti-vimentin | NA | 100.51 | 150.35 | 187.82 |

NA = Not applicable.

EXAMPLE 4

Utility of Different Detergents

Different detergents have been used in the preparation of the fixative composition of the present invention. The detergents were not only different in composition, but represent distinct classes of compounds. The fixative of the present invention was prepared as has been previously described, except in this experiment, the detergent and the detergent concentration were varied. The detergents used were polyoxyethylene ether W-1 (Polyox), polyoxyethylenesorbitans monolaurate (Tween 20), monopalmitate (Tween 40), monooleate (Tween 80) and polyoxyethylene 23 lauryl ether (Brij 35). Other detergents that work well include Nonidet P-40, Triton X-100, sodium deoxycholate and saponin.

In the present example, whole blood from a healthy donor was either resuspended in PBS/S or fixed with an equal volume of fixative reagent for 30 minutes at room temperature. All red blood cells from either fixed or live cell populations were removed by ammonium chloride lysis and the white blood cells washed twice by centrifugation (457× g, 21° C., 8 minutes) in PBS/S. The white blood cells were then immunostained using an indirect immunostain procedure and the antibody anti-vimentin (clone No. V9, Sigma Chemical Co.).

The T-cell tissue culture line CEM was used in addition to peripheral blood cells. Regardless of the fixative being tested, the method of fixation was as follows. CEM cells were pelleted (457×g, 21° C., 8 minutes), then washed twice by centrifugation (457×g, 21° C., 8 minutes) in PBS/S at room temperature. Washed cells were resuspended in PBS/S at a concentration of $2.5 \times 10^6$ cells/mL. The pool of cells was separated into 1 mL aliquots, then diluted with an equal volume of the appropriate fixative reagent. Cells were mixed and incubated for 30 minutes at room temperature. After 30 minutes, fixed cells were washed twice with 10 mLs of ice cold PBS. All cells were washed once more in PBS/S then resuspended to a concentration of $3.3 \times 10^6$ cells/mL.

Indirect Immunostain

Cells were reacted with the mouse monoclonal antibodies anti-gelsolin (clone No. GS-2C4, Sigma Chemical Co.) and anti-vimentin (clone No. V9, Sigma Chemical Co.). Immunostaining of cytoplasmic antigens was done by adding 5 uL of Control IgG2a mouse antibody (15 ug/mL), or 5 uL of anti-gelsolin (diluted 1/100 in PBS/S) or 5 ul of anti-vimentin (diluted 1/60 in PBS/S) to 100 ul of fixed or live cell suspension. Cells and antibody were incubated for one hour at 0° C., then washed twice in PBS/S using 2 mLs per wash. After the last wash, the supernatant fluid was removed by aspiration, and the cells resuspended in 250 uL of goat anti-mouse IgG-FITC conjugate (F(ab')$_2$, Sigma Chemical Co.) diluted 1/75 in PBS/S. Cells were again incubated on ice for 60 minutes, then washed three times in PBS/S, using 2 mL per wash. After the last wash, cells were resuspended in 0.5 mL of PBS/S and analyzed on a FACScan flow cytometer.

Immunostained cells, both live and fixed, were analyzed by flow cytometry. For both live and fixed cells, lymphocytes, monocytes and granulocytes were identified solely on the basis of their light scatter properties.

The addition of either polyoxyethylene ether or Brij™ 35 detergents lead to a dose-dependent increase in the percentage of fixed cells that bound anti-vimentin (Table E4-1). This increased cytoplasmic access was seen with all three cell types. More control antibody bound nonspecifically to monocytes and granulocytes than to lymphocytes. The elevated background staining seen with monocytes and granulocytes required the cut off between specific and nonspecific binding to be placed higher with these cell populations. This may explain in part why generally lower percentages of monocytes and granulocytes appear to have bound antibody, than identically treated lymphocytes. Polyox was more active than Brij™ 35 on a weight basis. No attempt was made to optimize the fixative reagent formulation around these detergents. Polyox, although very active as a cell permeabilization reagent had a profound effect on FSC of granulocytes and monocytes. The polyoxyethylene sorbitan detergents of the Tween series were examined because their structure was similar to polyox but they tend to be gentle detergents. The results of an experiment using CEM cells are shown in Table E4-2. A dose dependent increase in the percentage of cells that reacted with antibodies to the cytoplasmic antigens gelsolin and vimentin was seen with all three detergents. The ability to detect cytoplasmic antigens was dependent on not only the cells being fixed, but also on the concentration of detergent at the time of fixation. Tween 20 gave the greatest percent positive cells, followed by Tween 80 and finally Tween 40.

These data confirm that the immunologic detection of cytoplasmic antigens requires the cells be fixed. Fixation alone will impart only a limited ability to detect cytoplasmic antigens immunologically. The detection of cytoplasmic antigens is greatly improved by detergent treatment of cells; and fixation and detergent treatment may be done simultaneously in a single step. Fixation, followed by a separate permeabilization step is not required for successful retention and detection of cytoplasmic antigens. These data further support that a wide range of detergents may be employed for the purpose of permeabilizing cells. It is reasonable to speculate from these results that the detergent of the preferred embodiment may vary depending upon its intended use. For example, polyox may be the preferred detergent if the intended use requires good cell permeabilization but does not require preserving granulocyte FSC. It is further anticipated that some applications could require a combination of more than one detergent to achieve a desired performance.

TABLE E4-1

CELL TYPE AND THEIR PERCENT POSITIVE STAINING USING ANTI-VIMENTIN

| % DETERGENT | LYMPHO-CYTES | MONOCYTES | GRANULO-CYTES |
|---|---|---|---|
| LIVE CELLS | | | |
| 0.000 | 2.70 | 5.69 | 6.65 |
| POLYOX | | | |
| 0.003 | 25.47 | 9.65 | 8.57 |
| 0.006 | 32.68 | 22.49 | 12.82 |
| 0.018 | 44.54 | 39.35 | 29.51 |
| 0.036 | 67.22 | 68.85 | 51.71 |
| BRIJ 35 | | | |
| 0.003 | 15.34 | 5.50 | 7.42 |
| 0.006 | 24.61 | 8.33 | 14.07 |
| 0.018 | 20.74 | 12.46 | 15.58 |
| 0.036 | 27.57 | 13.10 | 22.00 |

PERCENT DETERGENT IS WEIGHT PER VOLUME.

TABLE E4-2

ABILITY OF DIFFERENT DETERGENTS TO MAKE CEM CELLS PERMEABLE TO ANTIBODY

| TREATMENT | DETERGENT % (W/V) | ANTI-GELSOLIN | ANTI-VIMENTIN |
|---|---|---|---|
| LIVE CELLS | NONE | 1.59 | 1.55 |
| FIXED CELLS | 0.000 | 25.26 | 27.48 |
| TWEEN 20 | 0.005 | 30.24 | 36.85 |
| | 0.010 | 43.28 | 37.42 |
| | 0.025 | 80.24 | 88.07 |
| | 0.050 | 96.67 | 93.96 |
| TWEEN 40 | 0.005 | 35.62 | 52.64 |
| | 0.010 | 47.87 | 50.75 |
| | 0.025 | 57.89 | 65.04 |
| | 0.050 | 68.79 | 51.93 |
| TWEEN 80 | 0.005 | 33.92 | 19.35 |
| | 0.010 | 28.11 | 42.57 |
| | 0.025 | 36.99 | 35.19 |
| | 0.050 | 89.51 | 90.65 |

EXAMPLE 5

Detection of the Human Immunodeficiency Virus in Infected Cells

Viruses grow within cells. The nucleic acids and proteins that constitute the viral particle are produced by the infected cell and accumulate in the cell. It should be possible to detect the presence of vital proteins in infected cells if the virus is transcriptionally active. The human immunodeficiency virus (HIV) produces many proteins. Some of the proteins regulate vital gene expression and some are structural proteins that make up the core or the envelope of the virus. The protein p24 is a structural protein that HIV infected cells produce in excess. The ability to detect replicating virus in cells may have clinical significance in detecting and monitoring the disease, acquired immunodeficiency syndrome (AIDS), caused by HIV. The virus load in HIV-infected individuals is related to disease progression and prognosis. In the past, and as previously described in the Background of the Invention, virus load has been monitored through the use of culture, polymerase chain reaction (PCR) or the p24 immunoassay. HIV culture and PCR are costly specialized tests, not amenable to most clinical laboratory environments. The p24 assay is often negative in HIV infected individuals, because immune complexes between p24 and the patient's own antibody prevent capture of p24 in commercial assay kits.

To determine if the reagents and methods of the present invention could be used to detect vital p24 within infected cells, HIV infected tissue culture cells and peripheral blood leukocytes from HIV infected individuals were examined. The human tissue culture cell line H9 is capable of supporting the growth of HIV. Uninfected H9 cells were obtained from the National Institutes of Health's AIDS Research and Reference Reagent Program. H9 cells, persistently infected with HIV, were obtained from the American Type Culture Collection. Uninfected and persistently infected H9 cells were grown in RPMI 1640 supplemented with 10% fetal bovine serum. Cultures were passed at least once per week. Blood from three individuals known to be infected with HIV was obtained and stored at room temperature in EDTA for less than 24 hours before being fixed. After fixation, the cells were frozen at −20° C. until thawed for an HIV p24 assay.

The fixative reagent was prepared as a 2× concentrate intended to be diluted with an equal volume of the cell suspension to be fixed. The 2× fixative reagent contained 1.44% formaldehyde, 73.0 mM DNBS, 15.0% DMSO and 50 uM (0.006%) NP40 detergent in phosphate buffered saline pH 7.2. The fixative was stored in amber glass bottles at room temperature until needed; usually less than 5 days. Uninfected and persistently infected H9 cells were pelleted (457×g, 21° C., 8 minutes), then washed once by centrifugation (457×g, 21° C., 8 minutes) in PBS at room temperature. Washed cells were resuspended in PBS at a concentration of approximately 1×10$^6$ cells/mL. Cells were then diluted with an equal volume of fixative reagent. Cells were mixed and incubated for 60 minutes at room temperature. After 60 minutes, fixed cells were washed twice with 10 mLs of ice cold PBS supplemented with 10% fetal bovine serum and 2% human AB serum (PBS/S), then resuspended to a concentration of 1×10$^6$ cells/mL.

Whole blood from a non-AIDS related hospital patient and each of three donors known to be infected with HIV was mixed for 60 minutes with an equal volume of fixative reagent. After 60 minutes at room temperature, fixed blood was washed twice in ice cold PBS/S. All red blood cells were removed by ammonium chloride lysis. The white blood cells were then immunostained using an indirect immunostain procedure.

Indirect Immunostain 200 uL of cell suspension was incubated with 20 ul of a mouse monoclonal antibody to HIV p24 (9A1B2, Ortho Diagnostic Systems) diluted 1:40 in PBS/S, or a rabbit polyclonal anti-p24 antibody (Chiron, Emeryville, Calif.) diluted 1:40 in PBS/S. Cells and antibody were incubated for one hour at 0° C., then washed twice in PBS/S. After the last wash, the supernatant fluid was removed by aspiration, and the cells resuspended in 200 uL of either goat anti-mouse IgG-FITC conjugate (F(ab')$_2$, Sigma Chemical Co.) diluted 1/75 in PBS/S or goat anti-rabbit IgG-FITC conjugate (F(ab')$_2$, Sigma Chemical Co.). Cells were again incubated on ice for 60 minutes, then washed three times in PBS/S. Cells used as negative controls were incubated with IgG2a control mouse antibody, normal rabbit serum, or no antibody at all. The cells were washed then incubated with goat anti-mouse-IgG-FITC or goat anti-rabbit-IgG-FITC. After the last wash, cells were resuspended in 1 mL of PBS/S and analyzed on a Cytofluorograph C50 flow cytometer.

Figure 4B:
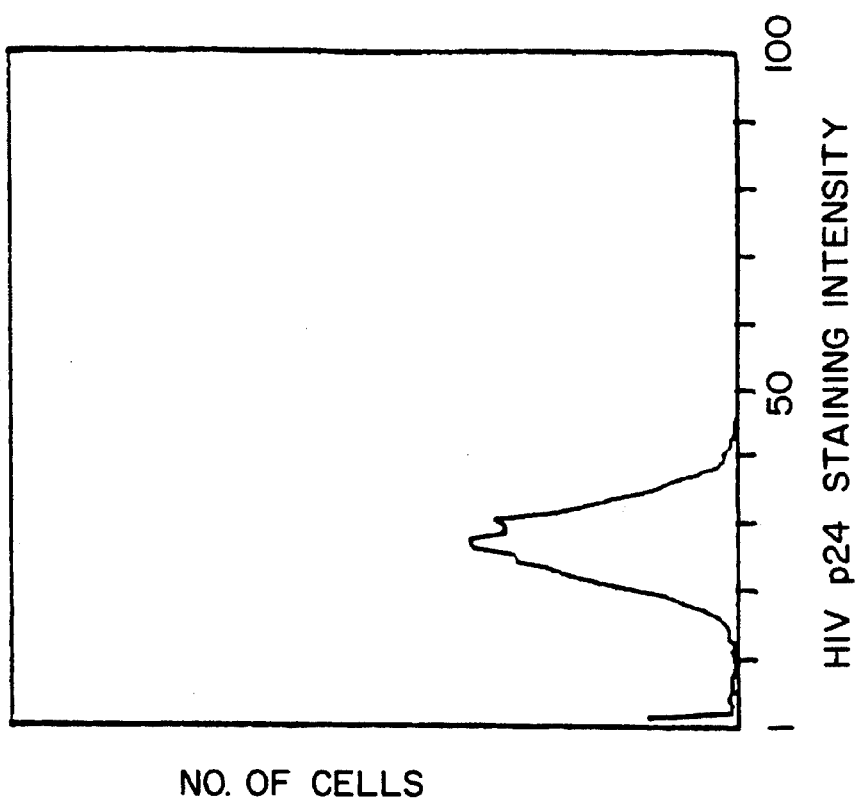
FIG. 4b is a histogram of the same data as depicted in 4a, plotting the number of cells versus the relative fluorescence intensity.
Figure 4A:
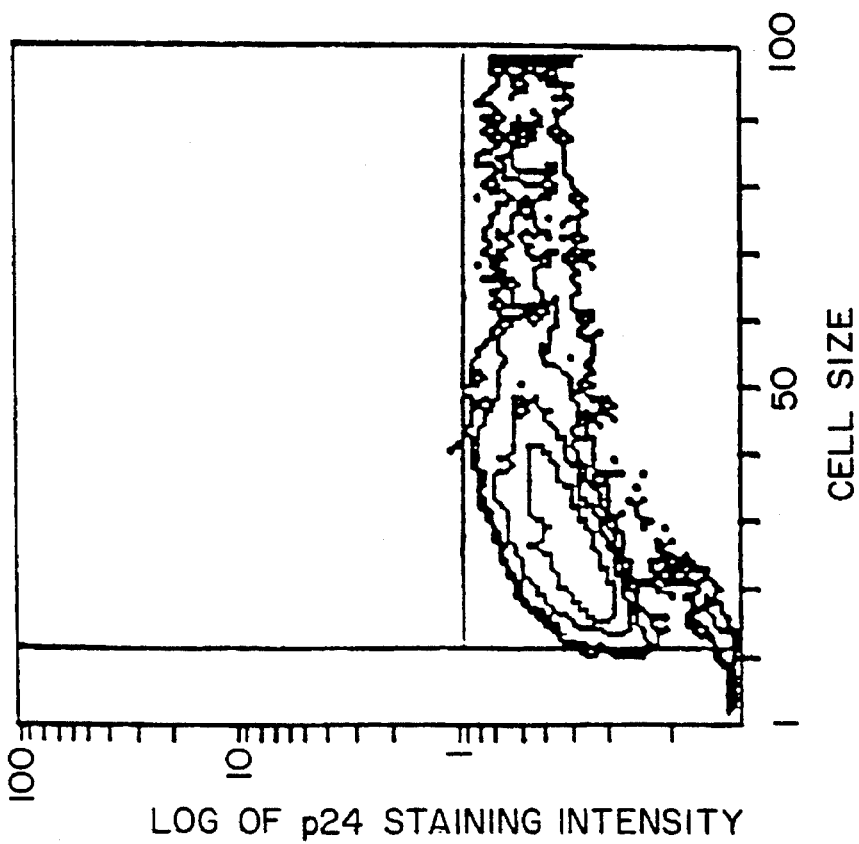
FIG. 4a is a contour plot, obtained with a FACScan, showing results of staining of uninfected cells reacted with anti-p24 monoclonal antibody.
Figure 5B:
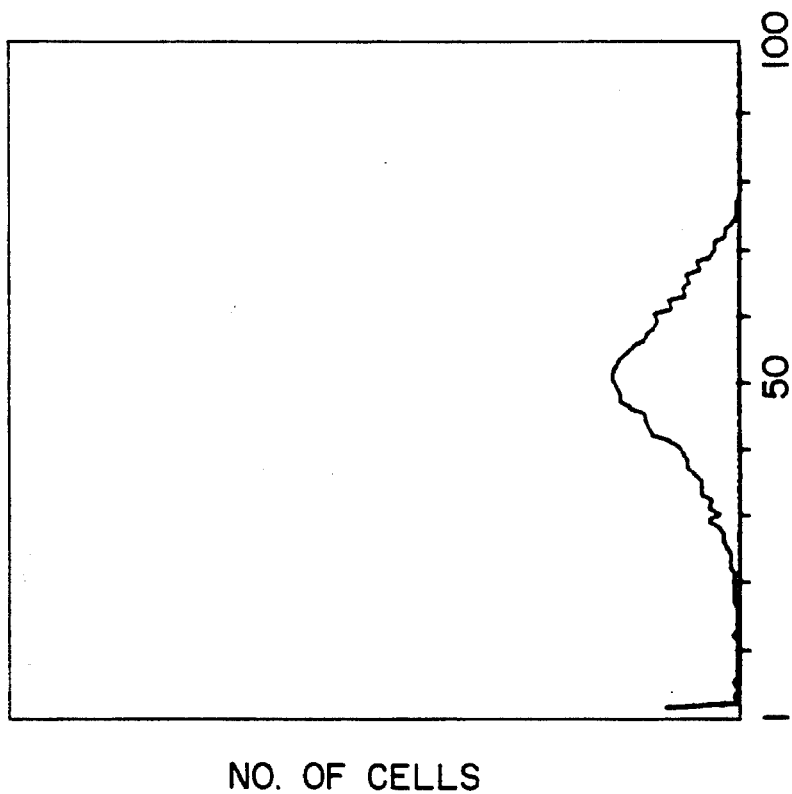
FIG. 5b is a histogram of the same data as presented in 5a, plotting the number of HIV-infected cells versus their relative fluorescence intensity.
Figure 5A:
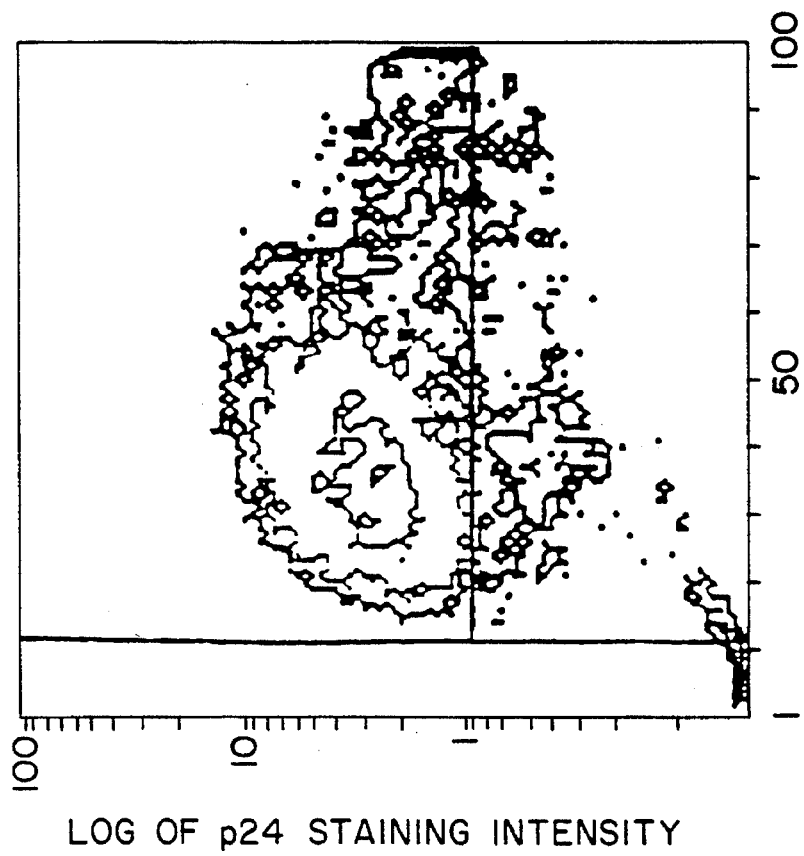
FIG. 5a is a contour plot, obtained with a FACScan, showing the results of staining of persistently HIV-infected cells reacted with anti-p24 monoclonal antibody.

The ability to detect HIV p24 in infected cells was demonstrated unequivocally using uninfected H9 and persistently infected H9 tissue culture cells (FIGS. 4a, 4b, 5a, and 5b). FIGS. 4a and 4b are uninfected cells reacted with anti-p24 monoclonal antibody. In FIG. 4a, the X-axis is FSC or cell size and the Y-axis is the fluorescence intensity of the anti-p24 staining. The data is presented as a contour plot. A contour plot is similar to the three-dimensional representations of data presented elsewhere in this application. In the case of a contour plot, the Z-axis or cell number is perpendicular to the plane of the paper. The observer views the data as if looking straight down on a "mountain" created by a cluster of events. As with geological relief maps, the contour lines represent slices through a peak at regular intervals. FIG. 4b is a histogram plotting the number of cells versus the relative fluorescence intensity; expressed as a percent of the maximum intensity. The log of the mean fluorescence intensity for uninfected H9 cells was 0.75. Only 1.2% of the H9 cells had a fluorescence intensity greater than 1.0. However, as seen in FIGS. 5a and 5b, when persistently HIV infected cells were treated with anti-p24 there was a marked increase in fluorescence intensity. The log of the mean fluorescence intensity for infected H9 cells was 3.27; and 86.2% of the H9 cells had a fluorescence intensity greater than 1.0. The binding of anti-p24 to p24 within the infected cells was also evidenced by the fluorescence intensity histogram, shown in FIG. 5b, shifting to the right when infected cells were used.

FIGS. 6a, 6b, 6c and 6d show the results when blood from HIV infected individuals and an uninfected control individual was tested. Side scatter was plotted on the X-axis and the fluorescence intensity of anti-p24 binding was plotted on the Y axis. Side scatter alone was not able to resolve monocytes from granulocytes in this experiment. This was most likely due to the cells having been frozen and thawed before being assayed. When patient cells had not been frozen and thawed prior to being used, light scatter could differentiate fixed lymphocytes, monocytes and granulocytes of HIV infected and AIDS patients as well as it could for uninfected individuals. FIG. 6a shows the result for a control HIV uninfected hospital patient. There is no evidence of anti-p24 antibody binding to cells in either the lymphocyte cluster on the left or in the monocyte-granulocyte cluster on the right. FIG. 6b shows the result from an individual classified as CDC stage III disease and taking the drug Zidovudine (AZT). The individual was asymptomatic at the time of blood draw. Note the distribution of the lymphocyte cluster is skewed upward on the Y-axis compared to the control cells. A number of lymphocytes bound a low level of anti-p24 in this patient. In addition, a cluster of a small number of brightly staining monocytes were clearly evident in this patient. FIG. 6c shows the results of an individual whose disease had progressed to CDC stage IV. This individual was suffering from oral candidiasis at the time the blood was drawn. In this patient the lymphocyte cluster was completely negative for anti-p24 binding. Granulocytes too seemed free of viral proteins but there was a striking involvement of the patient's monocytes. Finally, FIG. 6d presents the results of a patient with full blown AIDS. This individual had developed a peripheral neuropathy as a consequence of drug treatment and had to be removed from anti-retroviral chemotherapy. It was evident that numerous lymphocytes, monocytes and granulocytes bound anti-p24 antibody in this patient. Many cells bound so much anti-p24, their fluorescence was off scale.

These results demonstrate the methods and reagents of the present invention may be used for the immmunologic detection of viral proteins within infected cells. The surface differentiation markers on cells are preserved by the methods and reagents of the present invention, while also providing antibody access to internal antigens. It is possible to prepare a mixture of antibodies that contains an antibody to a cell surface differentiation marker with antibodies to internal antigens such as HIV structural proteins. For example anti-CD4-PE could be mixed with anti-p24-FITC. If such a mixture of antibodies was reacted with cells from an HIV infected individual, and examined on a flow cytometer, it would be possible to determine not only how many CD4 positive cells the individual had, but also how many of the CD4 positive cells were expressing viral p24 antigen. Such information may have prognostic or therapeutic value in the clinical management of HIV infection. It is obvious to those skilled in the art that this principle could be extended to other intrinsic or extrinsic cellular antigens, and is in no way limited to HIV or extrinsic pathogens.

EXAMPLE 6

Virus Inactivation Studies

Inactivation Of Rabbitpox virus

The fixative formulation and fixation methods of the present invention were tested for their ability to inactivate live virus. Three viruses were chosen for study; Rabbitpox, Simian virus 40 (SV40) and Human Immunodeficiency Virus type 1 (HIV-1). For these studies the fixative contained; 1.44% (w/v) formaldehyde, 73 mM dinitrobenzene sulfonic acid, 50 uM Nonidet P40 and 15% (v/v) dimethyl sulfoxide.

The Utrecht strain of Rabbitpox (ATCCVR-157) was used as the target virus. Vero cells (ATCC CCL 81) were used as the host cell for growing the virus. Vero cells were infected with Rabbitpox virus and incubated for 24 hours. Approximately $3 \times 10^7$ infected cells were washed, then resuspended in 1.0 mL of cell free Rabbitpox virus. The mixture was then diluted with 1.0 mL of fetal bovine serum to make the mixture 50% serum. A 0.1 mL sample was removed to test the total viral burden; this sample was labeled "Vital Load". The rest of the virus/cell suspension (1.9 mL) was mixed with 1.9 mL of fixative. A 0.1 mL sample was immediately removed and diluted 1:30 in EMEM+5% Tryptose Phosphate Broth (TSB). This represented the T=0 sample. The rest of the suspension was incubated 30 minutes at room temperature. At 30 minutes, a 0.1 mL sample was again taken and diluted 1:30 in EMEM+5% TSB, this represented the T=30 sample. Both the T=0 and T=30 samples were centrifuged to pellet cells. The supernatants were removed and kept on ice while the cell pellets were subjected to two rounds of freezing and thawing to lyse cells and release cell associated virus. The supernatant fluids were recombined with the lysed cell pellets and clarified by centrifugation to remove cell debris. The resulting supernatant fluids containing free and released virus were serially diluted and 0.1 mL samples inoculated into dishes containing uninfected Vero cells grown to confluence. The Vero cell cultures were incubated for 90 minutes at 36° C. to allow any live virus present to infect the cells. The cultures were then washed free of the vital inoculum, overlayed with medium containing agarose and incubated. Growth of the virus was quantitated by counting the number of plaques formed. All cultures were set up with appropriate positive and negative controls; and the results are expressed as the number of plaque forming units per mL (PFU/mL).

TABLE E6-1

Rabbitpox Inactivation.

| SAMPLE | DILUTION | PLAQUES/DISH | | | MEAN | PFU/mL |
|---|---|---|---|---|---|---|
| NEGATIVE | None | 0, | 0, | 0 | 0 | 0 |
| POSITIVE | $10^{-5}$ | 133, | 128, | 146 | 136 | $1.36 \times 10^8$ |
|  | $10^{-6}$ | 10, | 12, | 10 | 11 | $1.1 \times 10^8$ |
|  | $10^{-7}$ | 1, | 3, | 4 | 3 | $3 \times 10^8$ |
| Mean Viral Titer = $1.2 \times 10^8$ PFU/mL. | | | | | | |
| VIRAL LOAD | $10^{-4}$ | 451, | 422, | 434 | 436 | $4.36 \times 10^7$ |
|  | $10^{-5}$ | 55, | 59, | 50 | 55 | $5.5 \times 10^7$ |
|  | $10^{-6}$ | 8, | 8, | 11 | 9 | $9 \times 10^7$ |
| Mean Viral Titer = $4.9 \times 10^7$ PFU/mL. | | | | | | |
| T = 0 | $10^{-3}$ | 348, | 309, | 304 | 320 | $3.20 \times 10^6$ |
|  | $10^{-4}$ | 32, | 41, | 22 | 32 | $3.2 \times 10^6$ |
|  | $10^{-5}$ | 2, | 7, | 9 | 6 | $6 \times 10^6$ |
|  | $10^{-6}$ | 0, | 1, | 1 | 0.7 | $7 \times 10^6$ |
| Mean Viral Titer = $3.2 \times 10^6$ PFU/mL. | | | | | | |
| T = 30 | 1:30 | 0, | 0, | 0 | 0 | 0 |
|  | $10^{-2}$ | 0, | 0, | 0 | 0 | 0 |
|  | $10^{-3}$ | 0, | 0, | 0 | 0 | 0 |
|  | $10^{-4}$ | 0, | 0, | 0 | 0 | 0 |
|  | $10^{-5}$ | 0, | 0, | 0 | 0 | 0 |
| Mean Viral Titer = less than 90 PFU/mL. | | | | | | |

The total viral burden of the sample treated with fixative was $4.9 \times 10^7$ PFU/mL (Table E6-1). More than a log of virus was inactivated immediately on contact with the fixative as seen by the reduction to $3.2 \times 10^6$ PFU/mL in the T=0 sample. After 30 minutes of fixative treatment, no viable Rabbitpox virus could be detected. It is significant that even cell associated virus was killed; suggesting a viro-cydal concentration of fixative was able to penetrate Vero cells.

Inactivation of SV40 virus

The PA-57 strain of SV40 was used as the target virus. CV-1 cells (ATCC CCL 70) were used as the host cell for growing the virus. CV-1 cells were infected with SV40 virus and incubated for 72 hours. Approximately $2 \times 10^7$ infected cells were washed, then resuspended in 1.0 mL of cell free SV40 virus. The mixture was then diluted with 1.0 mL of fetal bovine serum to make the mixture 50% serum. A 0.1 mL sample was removed to test the total viral burden; this sample was labeled "Viral Load". The rest of the virus/cell suspension (1.9 mL) was mixed with 1.9 mL of fixative. A 0.1 mL sample was immediately removed and diluted 1:30 in EMEM+5% TSB. This represented the T=0 sample. The rest of the suspension was incubated 30 minutes at room temperature. At 30 minutes, a 0.1 mL sample was again taken and diluted 1:30 in EMEM+5% TSB, this represented the T=30 sample. Both the T=0 and T=30 samples were centrifuged to pellet cells. The supernatants were removed and kept on ice while the cell pellets were subjected to two rounds of freezing and thawing to lyse cells and release cell associated virus. The supernatant fluids were recombined with the lysed cell pellets and clarified by centrifugation to remove cell debris. The resulting supernatant fluids containing free and released virus were serially diluted and 0.1 mL samples inoculated into dishes containing uninfected CV-1 cells grown to confluence. The CV-1 cell cultures were incubated for 90 minutes at 36° C. to allow any live virus present to infect the cells. The cultures were then washed free of the viral inoculum, overlayed with medium containing agarose and incubated. Growth of the virus was quantitated by counting the number of plaques formed. All cultures were set up with appropriate positive and negative controls; and the results are expressed as the number of plaque forming units per mL (PFU/mL).

TABLE E6-2

SV40 Inactivation.

| SAMPLE | DILUTION | PLAQUES/DISH | | | MEAN | PFU/mL |
|---|---|---|---|---|---|---|
| NEGATIVE | None | 0, | 0, | 0 | 0 | 0 |
| POSITIVE | $10^{-5}$ | 65, | 69, | 82 | 72 | $7.2 \times 10^7$ |
|  | $10^{-6}$ | 7, | 11, | 7 | 8 | $8 \times 10^7$ |
| Mean Viral Titer = $7.2 \times 10^7$ PFU/mL. | | | | | | |
| VIRAL | $10^{-5}$ | 76, | 66, | 76 | 73 | $7.3 \times 10^7$ |

TABLE E6-2-continued

SV40 Inactivation.

| SAMPLE | DILUTION | PLAQUES/DISH | MEAN | PFU/mL |
|---|---|---|---|---|
| LOAD | $10^{-6}$ | 3, 4, 10 | 6 | $9 \times 10^7$ |
| Mean Viral Titer = $7.3 \times 10^7$ PFU/mL. | | | | |
| T = 0 | $10^{-5}$ | 153, 162, 183 | 166 | $1.66 \times 10^8$ |
|  | $10^{-6}$ | 28, 14, 26 | 23 | $2.3 \times 10^8$ |
| Mean Viral Titer = $2.0 \times 10^8$ PFU/mL. | | | | |
| T = 30 | $10^{-3}$ | 121, 98, 77 | 99 | $9.9 \times 10^5$ |
|  | $10^{-4}$ | 18, 9, 15 | 14 | $1.4 \times 10^6$ |
|  | $10^{-5}$ | 0, 0, 0 | 0 | 0 |
|  | $10^{-6}$ | 0, 0, 0 | 0 | 0 |
| Mean Viral Titer = $1.2 \times 10^6$ PFU/mL. | | | | |

The fixative inactivated SV40, but to a lesser extent than the Rabbitpox virus. Concentrations of fixative components, incubation time, and the like could be adjusted to enhance the virus inactivation capabilities. A maximum of one log of virus was inactivated by a 30 minute treatment with the fixative formulation tested.

Inactivation of HIV-1 virus

The HTLV-III-B strain of HIV-1 was used as the target virus. MT-4 cells were used as the host cell for growing the virus. MT-4 cells were infected with HIV-1 virus and incubated for 48 hours. Approximately $8 \times 10^6$ cells were pelleted, then resuspended in 0.8 mL of cell free HIV-1 virus. 0.4 mLs of this mixture was then diluted with 0.4 mL of fetal bovine serum to make the mixture 50% serum. A 0.1 mL sample was removed to test the total viral burden; this sample was labeled "Viral Load". The rest of the virus/cell suspension (0.7 mL) was mixed with 0.7 mL of fixative. A 0.1 mL sample was immediately removed and diluted 1:300 in RPMI 1640+10% FBS. This represented the T=0 sample. The rest of the suspension was incubated 30 minutes at room temperature. At 30 minutes, a 0.1 mL sample was again taken and diluted 1:300 in RPMI 1640+10% FBS, this represented the T=30 sample. Both the T=0 and T=30 samples were serially diluted and 0.1 mL samples inoculated into dishes containing 1.0 mL of uninfected MT-4 cells. The MT-4 cell cultures were not washed free of the inoculum, but cultures were fed twice per week by removing 1.0 mL of medium and replacing it with a fresh 1.0 mL. Cultures were examined on days 7, 14 and 28 post inoculation for the presence of cytopathic effect (CPE). Cytopathic effect is a morphologic change to an infected cell that occurs as a result of viral growth. In addition, supernatant fluids from 7, 14 and 28 day cultures were collected and assayed for the presence of HIV-1 specific viral p24 protein.

All cultures were set up with appropriate positive and negative controls; and the results are expressed as the percentage of inoculated wells containing CPE or the percentage of wells positive for p24 protein. The tissue culture infectious dose$_{50}$ (TCID$_{50}$) per mL was calculated using the formula TCID$_{50}$=A−(S$_f$/100−0.5) X B; where A=Log$_{10}$ of the highest concentration inoculated, S$_f$=sum of the percentage positive at each dilution and B=Log$_{10}$ of the dilution factor.

TABLE E6-3

HIV-1 Inactivation. CPE.

| | | % OF WELLS SHOWING CPE | | |
|---|---|---|---|---|
| SAMPLE | DILUTION | DAY 7 | DAY 14 | DAY 28 |
| NEGATIVE | None | 0 | 0 | 0 |
| POSITIVE | $10^{-5}$ | 0 | 100 | 100 |
|  | $10^{-6}$ | 0 | 50 | 100 |
|  | $10^{-7}$ | 0 | 50 | 100 |
|  | $10^{-8}$ | 0 | 0 | 25 |
|  | $10^{-9}$ | 0 | 0 | 0 |
| TCID$_{50}$/mL = | | $10^{5.5}$ | $10^{7.5}$ | $10^{8.75}$ |
| VIRAL LOAD | $10^{-5}$ | 100 | 100 | 100 |
|  | $10^{-6}$ | 25 | 100 | 100 |
|  | $10^{-7}$ | 0 | 25 | 100 |
|  | $10^{-8}$ | 0 | 25 | 100 |
|  | $10^{-9}$ | 0 | 0 | 0 |
| TCID$_{50}$/mL = | | $10^{6.75}$ | $10^{8.0}$ | $10^{9.5}$ |
| T = 0 | $1:3 \times 10^{-3}$ | 75 | 100 | 100 |
|  | $1:3 \times 10^{-4}$ | 0 | 100 | 100 |
|  | $1:3 \times 10^{-5}$ | 0 | 75 | 100 |
|  | $1:3 \times 10^{-6}$ | 0 | 50 | 75 |
|  | $1:3 \times 10^{-7}$ | 0 | 0 | 0 |
| TCID$_{50}$/mL = | | $10^{4.75}$ | $10^{7.25}$ | $10^{7.75}$ |
| T = 30 | $1:3 \times 10^{-2}$ | 0 | 0 | 100 |
|  | $1:3 \times 10^{-3}$ | 0 | 0 | 100 |
|  | $1:3 \times 10^{-4}$ | 0 | 0 | 25 |
|  | $1:3 \times 10^{-5}$ | 0 | 0 | 0 |
|  | $1:3 \times 10^{-6}$ | 0 | 0 | 0 |
| TCID$_{50}$/mL = | | $<10^{3.0}$ | $<10^{3.0}$ | $10^{5.25}$ |

TABLE E6-4

HIV-1 Inactivation. Viral p24 Protein.

| | | % OF WELLS POSITIVE FOR p24 | | |
|---|---|---|---|---|
| SAMPLE | DILUTION | DAY 7 | DAY 14 | DAY 28 |
| NEGATIVE | None | 0 | 0 | 0 |
| POSITIVE | $10^{-5}$ | 100 | ND$^a$ | ND |
|  | $10^{-6}$ | 100 | 100 | 100 |
|  | $10^{-7}$ | 100 | 100 | 100 |
|  | $10^{-8}$ | 100 | 100 | 100 |
|  | $10^{-9}$ | 100 | 100 | 100 |
| TCID$_{50}$/mL = | | $10^{10.5}$ | $10^{10.5}$ | $10^{10.5}$ |
| VIRAL LOAD | $10^{-5}$ | ND | ND | ND |
|  | $10^{-6}$ | 100 | 100 | 100 |
|  | $10^{-7}$ | 100 | 100 | 100 |
|  | $10^{-8}$ | 100 | 100 | 100 |
|  | $10^{-9}$ | 100 | 100 | 100 |
| TCID$_{50}$/mL = | | $10^{10.5}$ | $10^{10.5}$ | $10^{10.5}$ |
| T = 0 | $1:3 \times 10^{-3}$ | 100 | 100 | 100 |
|  | $1:3 \times 10^{-4}$ | 100 | 100 | 100 |
|  | $1:3 \times 10^{-5}$ | 100 | 100 | 100 |
|  | $1:3 \times 10^{-6}$ | 100 | 100 | 100 |
|  | $1:3 \times 10^{-7}$ | 100 | 75 | 100 |
| TCID$_{50}$/mL = | | $10^{9.0}$ | $10^{8.75}$ | $10^{9.0}$ |
| T = 30 | $1:3 \times 10^{-2}$ | 100 | 100 | 100 |
|  | $1:3 \times 10^{-3}$ | 100 | 25 | 100 |
|  | $1:3 \times 10^{-4}$ | 0 | 25 | 25 |
|  | $1:3 \times 10^{-5}$ | 0 | 25 | 0 |
|  | $1:3 \times 10^{-6}$ | 0 | 0 | 0 |
| TCID$_{50}$/mL = | | $10^{5.0}$ | $10^{4.75}$ | $10^{5.25}$ |

Treatment with the fixative for 30 minutes at room temperature inactivated between 4 and 5 logs of TCID$_{50}$ of HIV-1. It is noteworthy that virus not inactivated by the treatment was impaired significantly with regard to its growth kinetics. As can be seen from Table E6-3, on day 28 there was an estimated TCID$_{50}$=$10^{5.25}$/mL in the T=30 sample; yet no CPE was observed with this sample on days 7 and 14. In contrast, dilutions of the Virus Load and T=0 samples that contain comparable amounts of infectious virus ($10^{-5}$ or $10^{-6}$) did show CPE on days 7 and 14.

EXAMPLE 7

Immunostaining During Fixation

Fixative was prepared with the following formulation: 0.89% (wt/v) formaldehyde; 7.25% (wt/v) DMSO; 32 mM DNBS; 0.0998% (wt/v) Tween 20; 0.2 g/L $KH_2PO_4$; 0.2 g/L KCl; 2.16 g/L $Na_2HPO_4$.7 $H_2O$ and 4.2 g/L NaCl. Whole blood was collected by venipuncture in K3-EDTA and kept at room temperature until needed, usually less than 2 hours.

To 100 uL aliquots of whole blood was added antibodies to the cell surface antigens CD3 (OKT3), CD2 (OKT11), CD14 (OKM14) and control IgG; or to the cytoplasmic antigen vimentin (clone No. V9, Sigma Chemical Co.). Cells and antibodies were mixed and incubated at room temperature for 20 minutes, then 2 mL of the fixative formulation described above was added to each tube, mixed, and the cell suspension incubated for 40 minutes. After being fixed, cells were pelleted by centrifugation (457×g, 21° C., 8 minutes), the supernatant fluids were removed by aspiration and 3 mL of wash buffer (5% (v/v) Serum, 1.5% (w/v) bovine serum albumin and 0.0055% (w/v) ethylene diamine tetraacetic acid) added to each tube. Tubes were incubated for 10 minutes at room temperature. During this 10 minute incubation, red blood cells but not white blood cells lysed. White blood cells were then pelleted by centrifugation (457×g, 21° C., 8 minutes) and washed once more in 3 mLs of wash buffer. After being washed, cells treated with direct-labeled antibodies (control, OKT3, OKT11 and OKM14) were resuspended in 0.5 mL of PBS+2% formaldehyde and analyzed by flow cytometry. Cells that had been incubated with anti-vimentin were treated for 30 minutes at room temperature with 200 uL of goat-anti-mouse IgG coupled to FITC. These cells were washed two times with 3 mL of wash buffer, then resuspended in 0.5 mL of PBS+2% formaldehyde and analyzed by flow cytometry.

TABLE E7-1

| | | PERCENT POSITIVE CELLS | |
|---|---|---|---|
| TREATMENT | ANTIBODY | LYMPHO-CYTES | MONOCYTES |
| No fixation | Control IgG | 0.79 | 0.39 |
| | OKT3 | 67.92 | 3.62 |
| | OKT11 | 77.39 | 4.12 |
| | OKM14 | 0.12 | 82.31 |
| | Anti-vimentin | 1.34 | 6.47 |
| Fixed cells | Control IgG | 1.18 | 0.5 |
| | OKT3 | 66.19 | 0.15 |
| | OKT11 | 77.62 | 0.99 |
| | OKM14 | 0.34 | 88.37 |
| | Anti-vimentin | 91.14 | 95.20 |

As shown in Table E7-1, there was good agreement between the fixed and unfixed cells in the percentage of lymphocytes and monocytes reactive with antibodies to cell surface components. It is not possible to determine from this experiment how much of the cell surface staining took place during the 20 minute incubation before the addition of the fixative and how much occurred after fixative addition. However, it is reasonable to assume most of the cell surface reactivity occurred before the fixative was added. In contrast, reactivity with anti-vimentin could only have taken place in the presence of the fixative. Unfixed cells failed to react with anti-vimentin because the antibody could not gain access to the cytoplasmic location of the antigen. Addition of the fixative reagent however, fixed and permeablized the cells and gave anti-vimentin access to the cytoplasmic antigen. The antigen antibody interaction took place in the presence of the fixative reagent, and the specificity of the reaction was demonstrated by the failure of the control antibody to stain cells.

What is claimed:

1. A method for monitoring human immunodeficiency virus (HIV) infection in a patient so infected, comprising the steps of:
    a) contacting a sample of whole blood from said patient with a fixative composition in an amount and for a period of time effective to fix white blood cells present in said whole blood, without substantially destroying the ability of white blood cell antigens and viral components to bind ligands, wherein said fixative composition comprises:
        i) a first fixative compound selected from the group consisting of 2,4-dinitrobenzene sulfonic acid, 2,4-dinitrobenzoic acid, 2,4-dinitrophenol, and a combination of two or more of these;
        ii) a second fixative compound which is methanol-free, high-grade formaldehyde in a concentration ranging from about 0.1% to about 4%;
        iii) dimethylsulfoxide in a concentration of about 1% (v/v) to about 20% (v/v); and
        iv) a polyoxyethylene sorbitan surfactant in a concentration of about 0.001% to about 0.2% (w/v);
    b) isolating white blood cells present in said sample;
    c) either concurrently with the contact Step in a) or thereafter, contacting the cells so fixed with at least one antibody to a white blood cell antigen and at least one binding ligand that binds to at least one component from HIV;
    d) examining the scattering and fluorescent properties of said cells so fixed with a flow cytometer; and
    e) comparing the results of said examination to data obtained in the same manner from patients at various stages of HIV infection.

2. The method of claim 1 wherein said first fixative compound is 2,4-dinitrobenzene sulfonic acid.

3. The method of claim 1 wherein said at least one binding ligand that binds to said component from HIV is anti-p24 antibody.

4. The method of claim 1 wherein said at least one antibody to a white blood cell antigen is an anti-CD4 monoclonal antibody.

5. The method of claim 4 wherein said anti-CD4 monoclonal antibody is labelled with phycoerythrin and said anti-p24 antibody is labelled with FITC.

6. A reagent kit for monitoring HIV load in HIV-infected white blood cells, comprising:
    a) a fixative composition which comprises:
        i) a first fixative compound selected from the group consisting of 2,4-dinitrobenzene sulfonic acid, 2,4-dinitrobenzoic acid, 2,4-dinitrophenol, and a combination of two or more of these;
        ii) a second fixative compound which is methanol-free, high-grade formaldehyde in a concentration ranging from about 0.1% to about 4%;

iii) dimethylsulfoxide in a concentration of about 1% (v/v) to about 20% (v/v); and iv) a polyoxyethylene sorbitan surfactant in a concentration of about 0.001% to about 0.2% (w/v); and b) a binding ligand that binds to an intracellular antigen from HIV.

7. The reagent kit of claim 6 further comprising at least one antibody to a white blood cell surface antigen.

8. The reagent kit of claim 7 wherein at least one of said antibodies to a white blood cell surface antigen is a monoclonal antibody to CD4 positive T cells.

9. The reagent kit of claim 8 further comprising at least one monoclonal antibody to monocytes.

* * * * *